US011892381B2

(12) United States Patent
Mandal

(10) Patent No.: US 11,892,381 B2
(45) Date of Patent: Feb. 6, 2024

(54) METHODS, COMPOSITIONS, AND DEVICES INVOLVING PSEUDOKNOT FORMATION

(71) Applicant: Maumita Mandal, Pittsburgh, PA (US)

(72) Inventor: Maumita Mandal, Pittsburgh, PA (US)

(73) Assignee: Maumita Mandal, Pittsburgh, PA (US)

( * ) Notice: Subject to any disclaimer, the term of this patent is extended or adjusted under 35 U.S.C. 154(b) by 803 days.

(21) Appl. No.: 16/619,756

(22) PCT Filed: Jun. 5, 2018

(86) PCT No.: PCT/US2018/036018
§ 371 (c)(1),
(2) Date: Dec. 5, 2019

(87) PCT Pub. No.: WO2018/226666
PCT Pub. Date: Dec. 13, 2018

(65) Prior Publication Data
US 2020/0141839 A1 May 7, 2020

Related U.S. Application Data

(60) Provisional application No. 62/515,215, filed on Jun. 5, 2017.

(51) Int. Cl.
*G01N 1/22* (2006.01)
*B01L 3/00* (2006.01)
*C12N 15/113* (2010.01)
*C12N 15/115* (2010.01)

(52) U.S. Cl.
CPC ............ *G01N 1/2226* (2013.01); *B01L 3/50* (2013.01); *C12N 15/113* (2013.01); *C12N 15/115* (2013.01); *B01L 2300/025* (2013.01); *B01L 2300/0663* (2013.01); *C12N 2310/531* (2013.01)

(58) Field of Classification Search
CPC ... G01N 1/2226; B01L 3/50; B01L 2300/025; B01L 2300/0663; C12N 15/113; C12N 15/115; C12N 2310/531
See application file for complete search history.

(56) References Cited

U.S. PATENT DOCUMENTS

| | | |
|---|---|---|
| 7,347,925 B2 | 3/2008 | Hsieh |
| 7,756,560 B2 | 7/2010 | Frey et al. |
| 7,794,657 B2 | 9/2010 | Stewart |
| 7,888,292 B2 | 2/2011 | Bock et al. |
| 8,370,073 B2 | 2/2013 | Fernandez |
| 8,772,464 B2 | 7/2014 | Smolke et al. |
| 9,841,416 B2 | 12/2017 | Shepard et al. |
| 10,190,158 B2 | 1/2019 | Turner et al. |
| 10,271,738 B2 | 4/2019 | Peeters |
| 2002/0127623 A1 | 9/2002 | Minshull et al. |
| 2009/0082217 A1 | 3/2009 | Smolke et al. |
| 2010/0286082 A1 | 11/2010 | Breaker et al. |
| 2011/0263459 A1 | 10/2011 | Borer et al. |
| 2013/0012527 A1 | 1/2013 | Breaker et al. |
| 2013/0029342 A1 | 1/2013 | Breaker et al. |
| 2015/0093849 A1* | 4/2015 | Shepard ............ B01L 3/502707 438/49 |
| 2016/0016171 A1 | 1/2016 | Goel |
| 2018/0059101 A1* | 3/2018 | MacKay ............ G01N 33/5438 |

FOREIGN PATENT DOCUMENTS

WO WO2015089486 A2 6/2015
WO WO2017040946 A1 3/2017

OTHER PUBLICATIONS

Weeks et al. "A microcantilever-based pathogen detector," Scanning. Dec. 31, 2003 (Dec. 31, 2003), vol. 25, No. 6, pp. 297-299, entire document.
Goodson et al. "Integrating and amplifying signal from riboswitch biosensors," Methods in Enzymology, Jan. 8, 2015 (Jan. 8, 2015), vol. 550, pp. 73-91, entire document.
International Search Report and Written Opinion for Application No. PCT/US2018/036018, dated Oct. 15, 2018 (44 pages).

* cited by examiner

*Primary Examiner* — David C Thomas
(74) *Attorney, Agent, or Firm* — K&L Gates LLP

(57) ABSTRACT

Naturally occurring RNA pseudoknots fold into many topologies, yet their formation is poorly understood. Herein, by using high-resolution single-molecule force spectroscopy, the folding pathways of the H-type pseudoknot found in the preQ$_1$-riboswitch in *B. subtilis* were investigated By holding a single riboswitch RNA molecule in the optical-trap, the structural rearrangements as the end-to-end distance change along the pulling direction, x at a force, F were followed. The data reveal a multistate folding, wherein the intermediate hairpin undergoes a unidirectional conformational switching in the presence of ligand to form the pseudoknot receptor. Specifically-designed mutant RNAs resisted the switching mechanism and resulted in a significantly reduced pseudoknot population (4.5%) compared to the wild-type (100%). The free-energy landscape highlighted two kinetic barriers ($\Delta G^{\neq}$) that interrupt the folding pathway. By coupling the exothermic ligand-binding reaction ($\Delta G_{binding} = -16$ kT) to the folding events, the nascent transcript ensures successful barrier crossing, thus favoring the pseudoknot conformation.

11 Claims, 10 Drawing Sheets
Specification includes a Sequence Listing.

A

*wt aptamer*

B

*m1 aptamer*

C

*m3 aptamer*

SEQUENCE LISTING

<160> NUMBER OF SEQ ID NOS: 11

<210> SEQ ID NO 1
<211> LENGTH: 24
<212> TYPE: RNA
<213> ORGANISM: Artificial Sequence

```
<220> FEATURE:
<223> OTHER INFORMATION: chemically synthesized

<400> SEQUENCE: 1
ggagagguuc uagcuacacc cucu                                              24

<210> SEQ ID NO 2
<211> LENGTH: 22
<212> TYPE: RNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (6)..(17)
<223> OTHER INFORMATION: n is a, c, g, or u

<400> SEQUENCE: 2
agaggnnnnn nnnnnnnccu cu                                                22

<210> SEQ ID NO 3
<211> LENGTH: 25
<212> TYPE: RNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (4)..(22)
<223> OTHER INFORMATION: n is a, c, g, or u

<400> SEQUENCE: 3
uagnnnnnnn nnnnnnnnnn nncua                                             25

<210> SEQ ID NO 4
<211> LENGTH: 36
<212> TYPE: RNA
<213> ORGANISM: Artificial Sequence
<220> FEATURE:
<223> OTHER INFORMATION: chemically synthesized

<400> SEQUENCE: 4
ggagagguuc uagcuacacc cucuauaaaa aacuaa                                 36

<210> SEQ ID NO 5
<211> LENGTH: 24
<212> TYPE: RNA
<213> ORGANISM: Artificial Sequence
<220> FEATURE:
<223> OTHER INFORMATION: chemically synthesized

<400> SEQUENCE: 5
ggggagguuc uagcuacacc cccu                                              24

<210> SEQ ID NO 6
<211> LENGTH: 24
<212> TYPE: RNA
<213> ORGANISM: Artificial Sequence
<220> FEATURE:
<223> OTHER INFORMATION: chemically synthesized

<400> SEQUENCE: 6
ggagggguuc uagcuacacc cccu                                              24

<210> SEQ ID NO 7
<211> LENGTH: 36
<212> TYPE: RNA
```

```
<213> ORGANISM: Artificial Sequence
<220> FEATURE:
<223> OTHER INFORMATION: chemically synthesized

<400> SEQUENCE: 7
ggggagguuc uagcuacacc cccuauaaaa aacuaa                                36

<210> SEQ ID NO 8
<211> LENGTH: 36
<212> TYPE: RNA
<213> ORGANISM: Artificial Sequence
<220> FEATURE:
<223> OTHER INFORMATION: chemically synthesized

<400> SEQUENCE: 8
ggagggguuc uagcuacacc cccuauaaaa aacuaa                                36

<210> SEQ ID NO 9
<211> LENGTH: 49
<212> TYPE: DNA
<213> ORGANISM: Artificial Sequence
<220> FEATURE:
<223> OTHER INFORMATION: chemically synthesized

<400> SEQUENCE: 9
taatacgact cactataggg actggtgagt actcaaccaa gtcattctg                  49

<210> SEQ ID NO 10
<211> LENGTH: 30
<212> TYPE: DNA
<213> ORGANISM: Artificial Sequence
<220> FEATURE:
<223> OTHER INFORMATION: chemically synthesized

<400> SEQUENCE: 10
taggaagcag cccagtagta ggttgaggcc                                       30

<210> SEQ ID NO 11
<211> LENGTH: 20
<212> TYPE: DNA
<213> ORGANISM: Artificial Sequence
<220> FEATURE:
<223> OTHER INFORMATION: chemically synthesized

<400> SEQUENCE: 11
taatacgact cactataggg                                                  20
```

METHODS, COMPOSITIONS, AND DEVICES INVOLVING PSEUDOKNOT FORMATION

CROSS-REFERENCE TO RELATED APPLICATION

This application is a national stage application under 35 U.S.C. § 371 of PCT Application Serial No. PCT/US18/36018, filed Jun. 5, 2018, entitled METHODS, COMPOSITIONS, AND DEVICES INVOLVING PSEUDOKNOT FORMATION, which claims the benefit of U.S. Provisional Application No. 62/515,215, entitled MECHANISTIC FRAMEWORK OF PSEUDOKNOT FOLDING REVEALED BY SINGLE-MOLECULE FORCE EXPERIMENTS, filed Jun. 5, 2017, both of which are incorporated herein by reference in their entireties.

INCORPORATION BY REFERENCE OF SEQUENCE LISTING

This application contains a Sequence Listing in computer readable form (filename: 170447PCTUS sequence listing ST25.txt: 2,584 bytes-ASCII text file; created Dec. 5, 2019), which is incorporated by reference in its entirety and forms part of the disclosure.

FIELD

The present application discloses materials and methods related to folding routes and conformational transition states of biological molecules comprising one or more aptamer domains and applications utilizing the same.

BRIEF DESCRIPTION OF THE FIGURES

Various features of the embodiments described herein, together with advantages thereof, may be understood in accordance with the following description taken in conjunction with the accompanying drawings as follows:

FIG. 1A illustrates that the binding pocket in the wild-type (wt) aptamer is formed by three layers of conserved nucleotides. The primary layer is formed by the base quadruplex (C19-preQ1-A32-U9), wherein preQ1 in the binding pocket interacts with the loops L1, L2, and L3 via the residues U9, C19, and A32 respectively. The base quartet is further supported by a base triple above, C33-G13-A18 (P2-L2 interaction) and a base quadruple below formed by A30-G7-C20-A31 (P1-L3 interaction).

FIG. 1B illustrates that the P1A and P1 hairpins in the wild-type (wt) aptamer have near similar free energies ($\Delta G$). Thus, seemingly, both the hairpins are equally likely to form, unless external factors such as the presence of ligand, which can preferentially bind to a specific conformer over another. NMR studies indicate that the P1A helix forms in the absence of ligand (unbound conformation), whereas the P1-hairpin folds in the presence of preQ1 to form the pseudoknot receptor (bound conformation). For complete pseudoknot structure and sequence, see FIG. 2B.

FIG. 1C shows the theoretical free energies for the 5-bp P1 and the 3-bp P2. The two strands of P1 and P2 are connected by the GCAA tetraloop before evaluation by M-fold. The free energies indicated that the P1 helix is more stable than the P2 ($\Delta\Delta G=-6.5$ kcal/mol).

FIG. 4A (top) is a constant-force trace at 9.5 pN applied to a 36-nt queC mRNA structure. The grey and black curves depicted therein represent 4-kHz and 300-point smoothed traces, respectively. FIG. 2A (bottom) is a close-up view that shows fluctuations between U↔HP↔PK conformations of the 36-nt queC mRNA structure. The extension histograms are shown alongside. Dashed lines correspond to the theoretical worm-like-chain (WLC) distances.

FIG. 4B depicts an extension probability density, P(x) $nm^{-1}$ which confirms three conformational states (U, HP and PK) in the presence of $preQ_1$. The residual error is <1% in the deconvolution procedure.

FIG. 4C illustrates Force-dependent rate constants in the absence (0 µM) and presence (50 nM, 200 nM and 1 µM) of $preQ_1$. Data sets are fitted with Eq. 4. The open labels and the dashed lines indicate the folding reaction (U→HP→PK). The filled labels and the solid lines represent the unfolding pathway (PK→HP→U). The forward ($k_f$) and reverse ($k_u$) kinetics are shown in Table 1. Error bars represent mean±SD, n≥12 traces.

FIG. 7A illustrates that the 5' sequence can fold into one of the helical conformations (I or II). The conformers I and II corresponded to the P1A and P1 hairpins respectively. The complete pseudoknot sequence is not shown.

FIG. 7B illustrates force extension curves (FECs) for the wild-type (wt) queC mRNA and indicates a pseudoknot (PK) conformation in 0.2 µM preQ$_1$. The two lines represent the unfolding and refolding trajectories. Traces are fitted with the Eq. 1 (dashed). Percentage pseudoknot (PK) conformation is indicated for each condition. The minus sign represents absence of FECs that can be related to the PK conformation.

FIG. 7C illustrates that a mutant (m1) RNA folds into one stable hairpin structure that would normally resist a conformational change. The mutant (m1) RNA was created for this experiment and is not known to occur in nature.

FIG. 7D illustrates that a small fraction of the traces ~4.5% displayed the PK structure in saturating 200 µM preQ$_1$.

FIG. 7E illustrates that a mutant (m3) RNA can fold into three helical conformations I, II, III, whereby conformers I and II resembled P1A, while conformer III agreed with the P1 structure. The mutant (m3) RNA was created for this experiment and is not known to occur in nature.

FIG. 8A illustrates that the 36-nt queC mRNA from *B. subtilis* forms a compact 33-nt H-type pseudoknot structure upon binding preQ1, as shown by the NMR study discussed below.

FIG. 8B illustrates the mutant RNA (m1), where the A3U22 is replaced with G3C22 base pair. The mutant is designed to stabilize the lower region of the P1A helix (see FIG. 7 for the free energy discussion). Out of a total, n=242 traces analyzed in 200 µM preQ1, only 11 traces (4.5%) displayed the pseudoknot conformation, indicating that the hairpin switching from P1A→P1 is restricted in the mutant RNA (m1), which adversely affected the overall pseudoknot population. This data underscored that the hairpin rearrangement (P1A→P1) is important in the pseudoknot formation. The complete folding scheme is shown in FIG. 5.

FIG. 8C illustrates the mutant RNA (m3), which is essentially the reverse of the mutant RNA (m1). Here, the P1-stem is stabilized by replacing the A5, U22 with G5, C22 residues (see FIG. 7 for the free energy discussion). The mutant RNA (m3) exhibited 25%, 90% and 96% bound-pseudoknot conformation in 1 µM, 10 µM and 200 µM preQ1, respectively, suggesting that the half-maximum binding (KD) lies between 1-10 µM. The change in the binding affinity may be attributed to the weak tertiary interaction between L3-P1 that may have affected the overall stability of the binding pocket.

FIG. 9A illustrates a representative trace for the mutant (m3) RNA exhibiting hopping between U↔HP↔PK in 10 µM preQ$_1$. The extension vs. time trace was recorded at the equilibrium force, $F^{eq}$~12 pN. The dashed lines represent the theoretical distances for U, HP, and PK conformations, following the worm-like-chain (WLC) equation, discussed below.

FIG. 9B illustrates a distance histogram that exhibited fluctuations between the U↔HP and HP↔PK conformations with peak maximum extensions at 8.2±0.01 nm (mean±standard deviation) and 12.4±0.01 nm, respectively, that indicated the formation of the hairpin (20±1.5 nucleotides) and the pseudoknot (30.4±1.5 nucleotides) structures, respectively. The Gaussian mean overlapped with the calculated average within the error range.

FIG. 10A (Upper) illustrates isothermal titration for preQ$_1$ binding to the wt RNA in Ca$^{2+}$ buffer. FIG. 10A (Upper Inset) shows thermodynamic parameters ΔG (kcal/mol), ΔH (kcal/mol), ΔS (cal/mol/deg) and K$_D$ (nM) in Ca$^{2+}$ and Mg$^{2+}$ buffers. Note that ΔG$_{binding}$ remained constant irrespective of the buffer. FIG. 10A (Lower) illustrates binding isotherms in Mg$^{2+}$ (top curve) and Ca$^{2+}$ buffer (bottom curve). Error bars represent standard deviation from three independent experiments.

FIG. 10B illustrates the average free energy landscape (top curve) for the wt RNA and is plotted along the folding distance (x-axis) for the reaction U→HP→PK. The grey shaded region indicates SD±1 kT. The transition distances ($\Delta x^{\ddagger}$) are measured from the linear state (U), which agrees with the calculated distances (Table 1). The bottom curve indicates the preQ$_1$-binding ($\Delta G_{binding}$). The conformations for linear (U), hairpin (HP) and pseudoknot (PK) states are schematically drawn.

FIG. 10C shows the average free energy landscape for m3 at 11.5 pN, 12.0 pN, and 12.5 pN (SD±1kT). The plot shows a sharp hairpin barrier ($\Delta G^{\ddagger}_{HP}$), which explains the requirement of high preQ$_1$ to induce a pseudoknot structure. The $\Delta G_{binding}$ for the mutant (m3) RNA was similar to the wt RNA.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
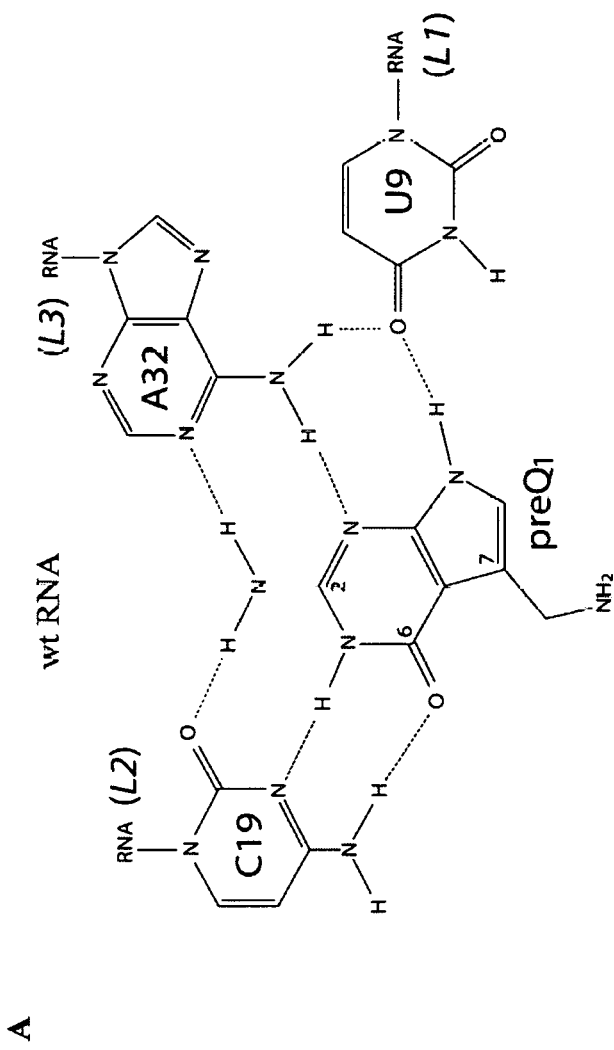
FIGS. 1A-1C illustrate the hydrogen-bonding interactions and the hairpin stabilities in a wild-type (wt) aptamer.
Figure 1:
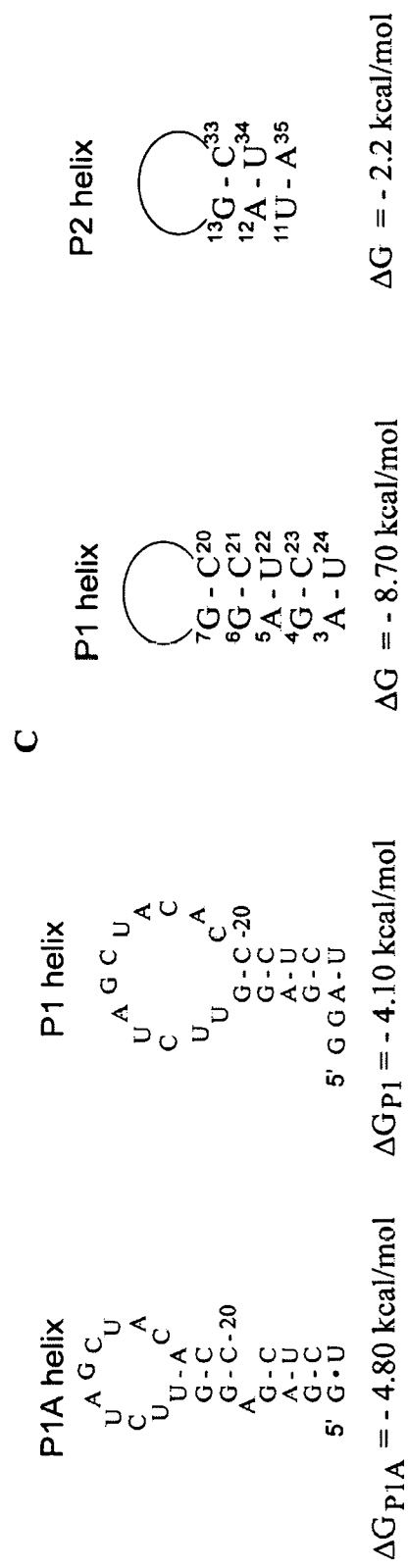

The mechanism by which ribonucleic acid (RNA) forms pseudoknot structures is a highly debated topic, although their biological roles in gene regulation is undisputed. Studies indicate that RNA pseudoknots are explicitly involved in the translational repression, ribosomal frameshifting, telomerase and ribozyme activities; yet our understanding of the folding mechanisms and the self-assembly of the knotted structures is poor. Biochemical experiments such as ultraviolet (UV) melting profiles and calorimetric studies have provided insights on the overall stabilities of RNA pseudoknots; however, due to the low resolution of the techniques, the intermediate states, kinetics and energetics were unresolved until now. The problem is further compounded as RNA secondary structures are dynamic in physiological buffer conditions, thus the identification of transition states can be extremely challenging by bulk biochemical methods. In the absence of direct evidence, our current knowledge of pseudoknot folding is largely based on theoretical models that have suggested hairpin structures as the intermediate state, for instance, the hepatitis delta virus ribozyme. Monte Carlo simulation studies have further suggested that conformational switching between two structurally related hairpins can occur through pseudoknot assisted pathway based on the position of the guanine-cytosine (GC) stacks.

Recent single-molecule force measurements have proven to be a powerful tool toward dissecting the folding pathways in complex structures by nucleic acids and proteins. By applying a calibrated tension on one molecule, the folding properties, such as the intermediate state, dwelling time ($\tau$, sec), and the inter-conversion rates (k, sec$^{-1}$), have been successfully defined along the reaction coordinate that were previously inaccessible by biochemical methods. Noticeably, the reaction coordinate in mechanical experiments is one-dimensional, whereby the end-to-end linear distance of the polymer chain is dependent on the applied force (F) along the pulling direction, x. If measured carefully, the net extension changes during the conversion from folded→unfolded state can then be related to a serial worm-like-chain (WLC) model. Recent mechanical experiments have shown that the folding path by which a RNA molecule approaches the final conformational state is largely dictated by the loading rate (pN/s) and the mode of applied tension. To elaborate this further, a 49-nt P5ab RNA hairpin was subjected to a range of pulling forces. The hairpin displayed the characteristic two-state transition (folded↔unfolded) at slow (2 pN/s) and fast loading rates (16 or 32 pN/s). However, at the optimum loading rate, 7.6 pN/s (or 200 nm/s), the hairpin exhibited multiple intermediate states (I$_1$, I and I$_2$) both in the unfolding and the refolding pathways. Interestingly, the intermediate states were also recognized at similar distances, when the hairpin was held at a constant-force near equilibrium. Here, a custom-built high-resolution optical-tweezers system (FIG. 2A) was used to investigate the folding pathways in the H-type pseudoknot. With this optical tweezers system, single base pair fluctuations (~1 nm) at sub-piconewton forces (±0.1 pN) were successfully resolved with high accuracy and precision thereby revealing the formation of RNA pseudoknot structures.

Figure 2:
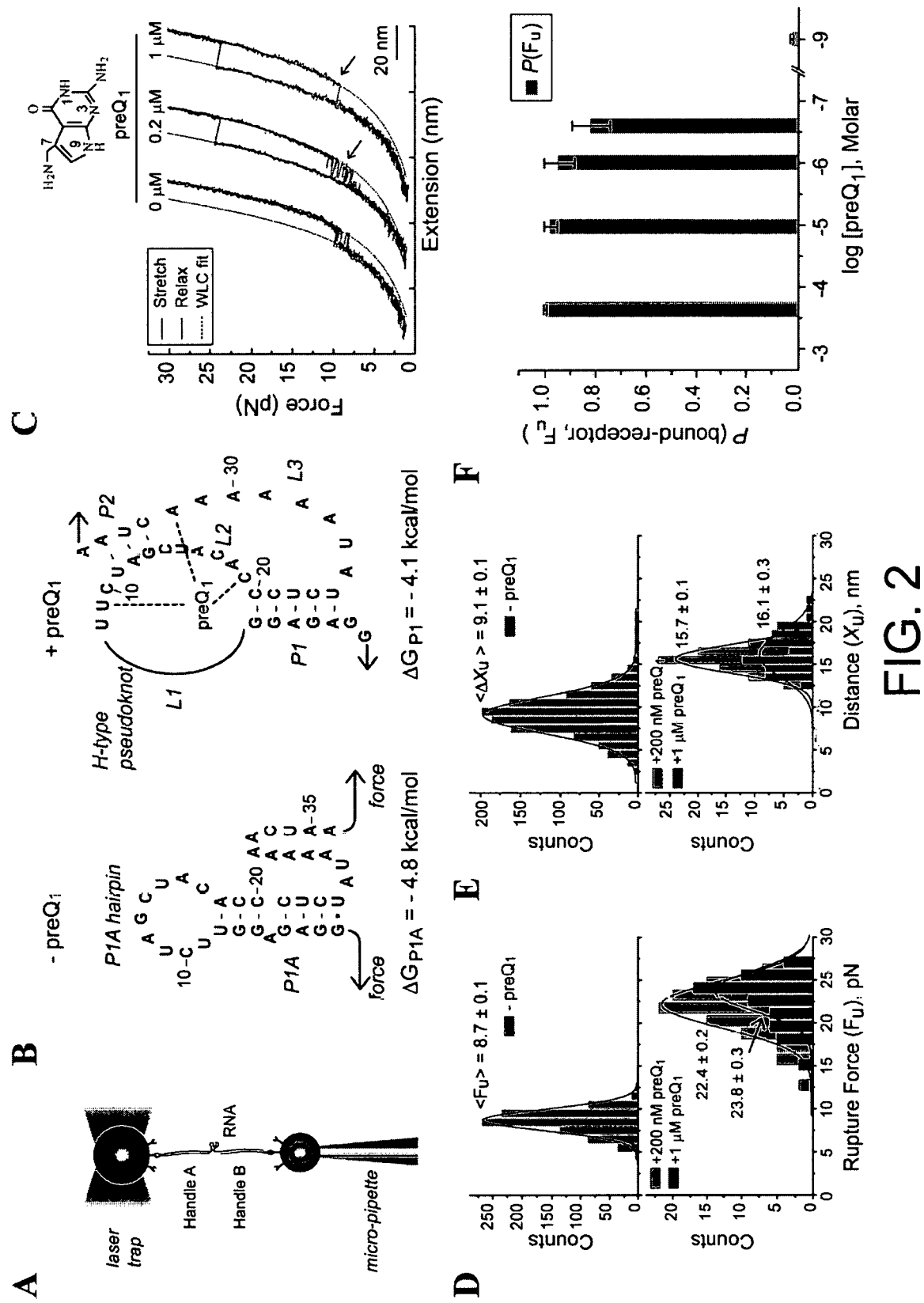
FIG. 2A is a diagram illustrating an experimental set-up in an optical tweezers instrument in accordance with at least one embodiment.
FIG. 2B is a sequence and secondary structure for 36-nt queC mRNA. The RNA forms a 24-nt P1A hairpin in the absence of $preQ_1$ (left). In the presence of $preQ_1$ (right), the 33-nt H-type pseudoknot structure with helices (P1, P2) and loops (L1, L2, and L3) is formed. The ligand is held tightly in the binding pocket through $C_{19}$-$preQ_1$-$U_9$-$A_{32}$ hydrogen bond interactions. The arrows indicate the pulling direction in the optical trap.
FIG. 2C illustrates force extension curves in the absence (0 µM) and presence of $preQ_1$ (0.2 µM, 1 µM). The loading rate is 7.6 pN/s. The unfold (stretch) and refold (relax) trajectories are shown with different curves. Traces are fitted with Eq. 1 (dashed lines), discussed below. Arrows indicate bi-stabilities or the refold transition near 10 pN.
FIGS. 2D and 2E illustrate rupture force ($F_u$) and distance ($\Delta X_u$) histograms, respectively, in the absence (n=102 traces) and the presence of $preQ_1$ (n=126 traces in 0.2 µM $preQ_1$; n=83 traces in 1 µM $preQ_1$). The standard error of the mean (±SEM) is indicated against fitted Gaussian curves.
FIG. 2F is a probability distribution of the bound-receptor conformation, $P(F_u)$ is determined from the unfolding traces. The aptamer showed 90% occupancy in 0.2 µM $preQ_1$ (n≥90 traces).

Toward this end, the 36-nt queC preQ$_1$ riboswitch (FIG. 2B) from B. subtilis was employed. It has been shown that 36-nt queC preQ$_1$ RNA formed a compact H-type pseudoknot structure in the presence of the metabolite preQ$_1$. Apparently, the preQ$_1$-induced pseudoknot downregulates the expression of the queC operon by allowing transcription termination. According to nuclear magnetic resonance (NMR) and X-ray studies, the pseudoknotted structure comprises of P1, P2 helices, which are inter-connected by loops L1, L2, and L3 as shown in FIG. 2B. The binding pocket is stabilized by three layers of conserved nucleotides that forms extensive H-bonding with the ligand. The primary layer is formed by the base quadruplex $C_{19}$-preQ$_1$-$A_{32}$-$U_9$ (FIG. 1). The base quartet is further supported by a base triple on the top, $C_{33}$-$G_{13}$-$A_{18}$ (P2-L2 interaction) and a base quadruple below, $A_{30}$-$G_7$-$C_{20}$-$A_{31}$ (P1-L3 interaction). In the absence of the ligand, the queC mRNA reportedly forms a 24-nt long P1A hairpin. M-fold analyses showed that the P1A and P1 helices have competitive free energies, −4.80 kcal/mol and −4.10 kcal/mol respectively (FIG. 1), although the two hairpins form under different conditions. Alternatively, this implied that only P1 helix could accommodate the H-type pseudoknot conformation, despite the fact the P1A and P1 both have similar free energies. It was realized that the structurally related P1A and P1 hairpins undergo conformational switching that has not been reported so far. Hence, the complete folding mechanism in the queC mRNA that leads to the pseudoknot architecture by using single-molecule force spectroscopy was investigated. This investigation has produced methods, compositions, and devices as described herein.

Results

Mechanical Pulling Traces Revealed the Pseudoknot Conformation

The wild-type (wt) 36-nt preQ$_1$ riboswitch RNA was subjected to force-dependent denaturation and renaturation at a constant pulling speed (CS). The optimum loading rate was determined as 7.6 pN/s. The resulting force-extension curves (FECs) from pulling a single RNA molecule in the presence and absence of ligand is shown in FIG. 2C. In the absence of preQ$_1$ (0 μM), the wt RNA displayed a reversible unfold-refold trajectory with hopping at a low force, $F_u$=8.7±0.1 pN (mean±SE, n=102 traces, FIG. 2D). Considering 0.37 nm as the inter-nucleotide distance following a serial worm-like-chain model, see Eq.1 below, the hopping distance $\Delta X_u$=9.1±0.1 nm corresponded to the melting of 24.3±0.3 nucleotides (nts). This suggested a 24-nt P1A helical structure in the absence of the ligand, which is consistent with the NMR study. In the presence of 200 nM preQ$_1$, a distinct unfold transition was observed at a higher force, F$_u$=22.4±0.2 pN. The rupture distance, ΔX$_u$=15.7±0.1 nm corresponded to the unfolding of 34.1±0.2 nts, indicating the 33-nt pseudoknot conformation (FIGS. 2C, 2D, 2E). Thus, the single-molecule results were consistent with the NMR report. All measured distances agreed with the theoretical values following Eq. 1 (Table 2). At 1 μM preQ$_1$, the unfold transition shifted to 23.8±0.3 pN, although ΔX$_u$ remained unperturbed within the error margins (FIGS. 2D, 2E). The data indicated that the H-type pseudoknot formed by the queC mRNA is mechanically stable, which can resist unfolding to high forces. Similar mechanical stabilities have been reported for other RNA pseudoknots involved in ribosomal frameshifting. The probability distribution for a bound-pseudoknot receptor during unfolding, P(F$_u$) is plotted in FIG. 2F. The plot underscores that the riboswitch is predominantly bound ~90% in 200 nM preQ$_1$. Previous in-line probing has indicated that the queC mRNA binds preQ$_1$ with apparent K$_D$~50 nM.

Unlike the unfolding curves described above, the refold trajectories (FIG. 2C) in 200 nM preQ$_1$ displayed hopping near 10 pN. Furthermore, the bi-stabilities were replaced by a distinct refold transition in 1 μM preQ$_1$ (FIG. 2C). It was construed that the hopping behavior observed during refold may be indicative of the "ON-OFF" binding kinetics (k$_{on}$/k$_{off}$). To assess this further, the constant-force (CF) assay was performed (FIG. 4A).

Pseudoknot Formation Follows Multi-State Transition

In the constant speed (CS) pulling mode described above, the rupture and the formation of bonds between two complementary helical strands follow a non-equilibrium process that could be influenced by the loading rate as shown for P5ab hairpin previously. However, in the constant force (CF) mode (whereby, the loading rate is zero), a tethered RNA molecule with any secondary structure can be controlled to hop between the folded and the unfolded conformations. In fact, near equilibrium (F$^{eq}$), the hopping can continue indefinitely as the forward and reverse rates are equal (k$_f$=k$_u$). Such experiments offer incredible insights on the dwell time (τ), which is related to the kinetic rates (k) by the relation, k=1/τ. In the above-discussed optical tweezers, fluctuations can be observed due to the structural rearrangements of the riboswitch RNA for long durations (>250 sec) with minimal drift. This allowed short-lived intermediate states to be identified that are otherwise masked by noise. Therefore, the queC riboswitch was held at a low force near 10 pN to observe its conformational rearrangements in real-time as the linear RNA transitioned to the pseudoknot structure. By employing a similar approach, the long-range tertiary kissing interactions in the folding of the purine riboswitch were identified.

Figure 3:
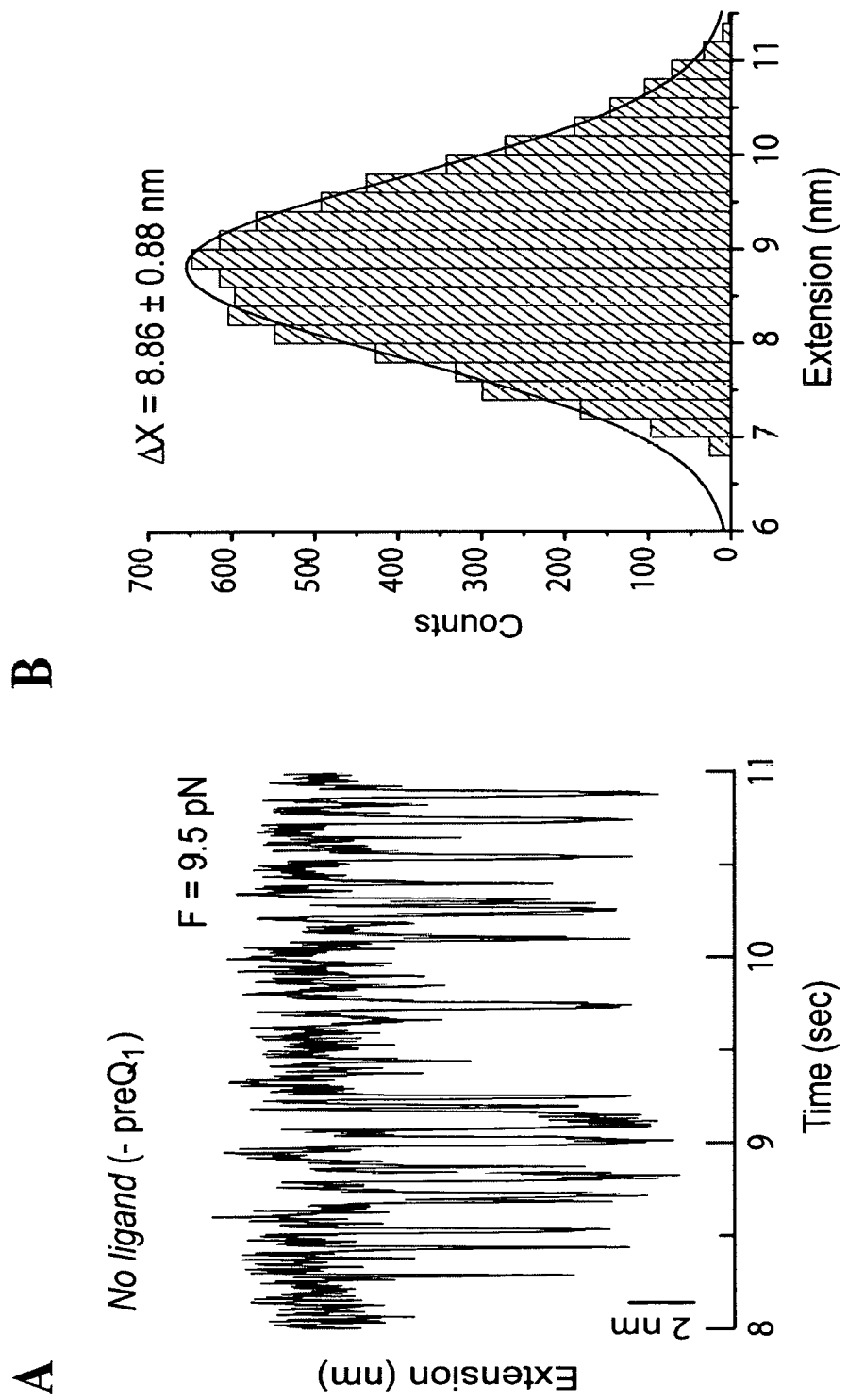
FIG. 3A is a trace depicting the typical unsmoothed extension of the 36-nt queC RNA structure in the absence of preQ1 at a constant 9.5 pN vs. time. Data is recorded at 4 kHz sampling rate.
FIG. 3B is an extension histogram for a 40-sec window indicating the average extension change as, $\Delta X=8.9\pm0.88$ nm (mean±SD). Following the serial worm-like-chain (WLC) equation (Eq. 1), the extension change corresponded to the unfolding of 23.4±2.3 nucleotides. Thus, this data is consistent with the NMR report suggesting a 24-nucleotide P1A hairpin in the absence of preQ1.
Figure 4:
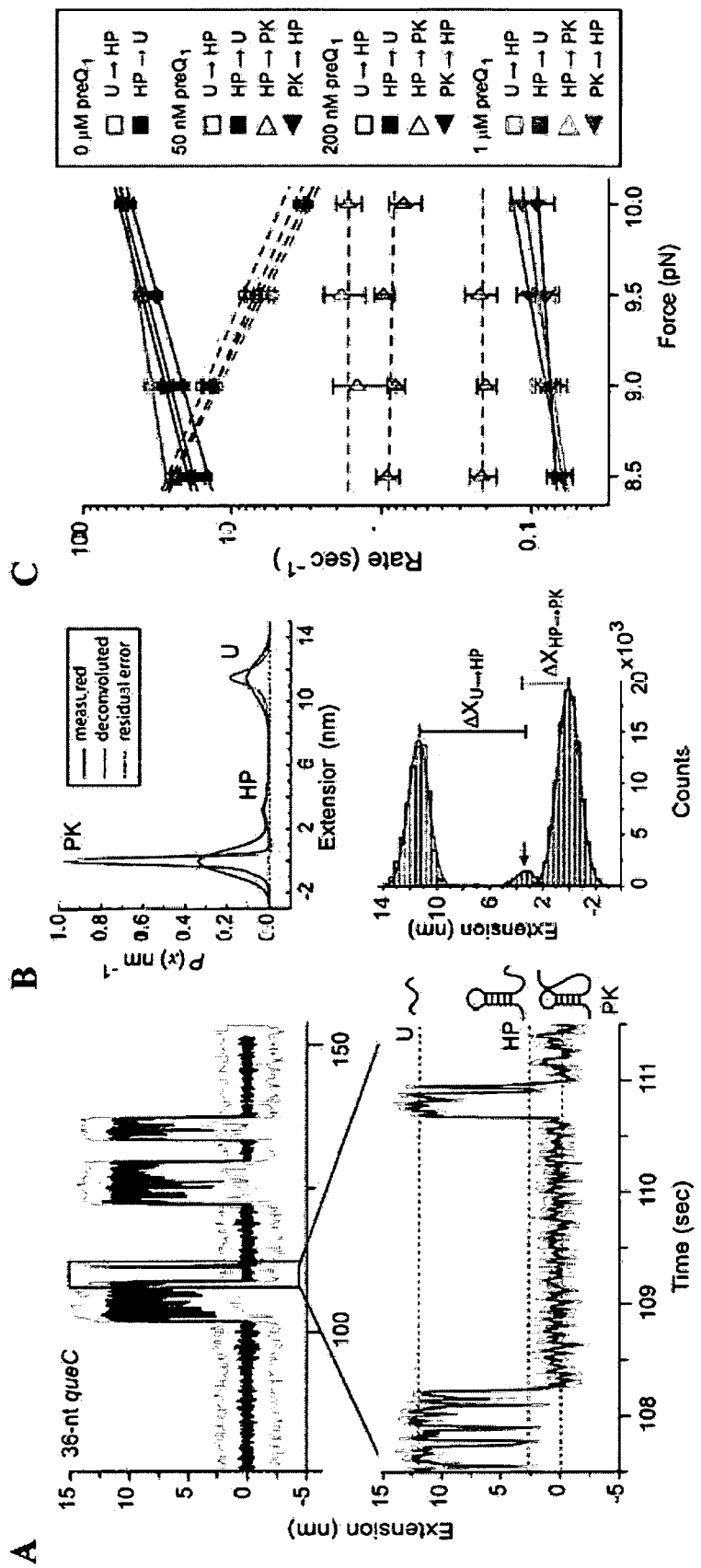
FIGS. 4A-4C illustrate that $PreQ_1$ induces the H-type pseudoknot conformation in the queC mRNA.

A typical extension vs. time trace in 200 nM preQ$_1$ is shown in FIG. 4A. The trace shows a three-state transition, wherein the linear (U) mRNA first folded into the hairpin (HP) conformation, which was then followed by the 33-nt pseudoknot (PK). The measured distances and the probability density, P(x) (FIG. 4B, Table 1) supported a three-state transition. The CF traces reveal that the pseudoknot formation progresses in the 5'→3' direction, wherein the 5-bp P1 helix folds first, followed by the 3-bp P2. Thermodynamically, the 5-bp P1 stem is more stable than P2 (ΔΔG=−6.5 kcal/mol), hence such a folding scheme is plausible (FIG. 1). In this direction, recent MD simulations have also indicated that the helix stabilities can determine the folding direction in the formation of pseudoknotted structures. In the absence of preQ$_1$, the folding was restricted up to the P1A hairpin (U↔HP), which is evident from the traces and the measured distances (FIG. 3, Table 1). This clearly suggested that the presence of the ligand preQ$_1$ is the essential driving force in the formation of the pseudoknot in the queC mRNA.

Force-Dependent Folding Kinetics (k) For Secondary and Tertiary Structures

The pseudoknot folding reaction shown in FIG. 4A can be expressed as,

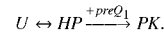

$$U \leftrightarrow HP \xrightarrow{+preQ_1} PK.$$

Near equilibrium (F$^{eq}$~9 pN), the forward (k$_f$) and the reverse (k$_u$) rates for the U↔HP reaction were measured as 6.4±0.2 s$^{-1}$ and 41.7±0.8 s$^{-1}$ respectively (n=24 traces; Table 1), which is typical for short hairpins. It is noteworthy, that the equilibrium is force-dependent, hence the kinetic rates are strongly affected even by an incremental change in the applied tension. The force-dependent rates, k(F) from 8.5 pN to 10.0 pN were measured in the absence and presence of 50 nM, 200 nM and 1 μM preQ$_1$. The data sets (mean±standard deviation (SD)) are shown in FIG. 4C. The folding and unfolding kinetics were fitted with the Bell's relationship, $$k(F) = k_0 \exp\frac{F\Delta x^\ddagger}{k_B T},$$

where k$_0$ is the intrinsic rate, Δx$^\ddagger$ is the transition distance, k$_B$ is the Boltzmann constant and T is the temperature (see Eq. 4 below for more details). The plot highlights that the forward (k$_{U \rightarrow HP}$) and the reverse (k$_{HP \rightarrow U}$) rates for the hairpin folding are unperturbed by the presence or absence of the ligand. As a result, the F$^{eq}$ wherein k$_f$=k$_u$ superposed at 8.6 pN regardless of the preQ$_1$ concentrations in the buffer.

The subsequent conversion from the hairpin to the pseudoknot structure

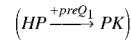

$$\left(HP \xrightarrow{+preQ_1} PK\right)$$

revealed some important features. Foremost, the reaction proceeded with k$_{ON}$=1.0±0.1 s$^{-1}$ and k$_{OFF}$=0.08±0.01 s$^{-1}$, which was slower compared to the hairpin kinetics (FIG. 4C, Table 1). This may be attributed to the folding of the otherwise flexible 3'-A rich tail into the H-type pseudoknot conformation. Secondly, the conversion was strictly dependent on the preQ$_1$ concentrations. Thus, k$_{ON}$ increased 10-fold from 0.2 s$^{-1}$ in 50 nM preQ$_1$ to 2 s$^{-1}$ in 1 μM preQ$_1$. The data suggests that the rate of ligand-association in *B. subtilis* preQ$_1$ aptamer is faster by ~10-fold (k$_{ON}$=1.0±0.1 s$^{-1}$) compared to the *F. nucleatum* aptamer (0.12 s$^{-1}$ at 200 nM preQ$_1$ or 6.0×10$^5$ M$^{-1}$s$^{-1}$). For the latter, the rates were measured by fluorescence spectroscopy. However, the dissociation rates (k$_{OFF}$) are similar for both the aptamers (0.08±0.01s$^{-1}$ in *B. subtilis*; 0.08 in *F. nucleatum*).

PreQ$_1$ Induces Hairpin Switching from P1A→P1 Helix

Figure 5:
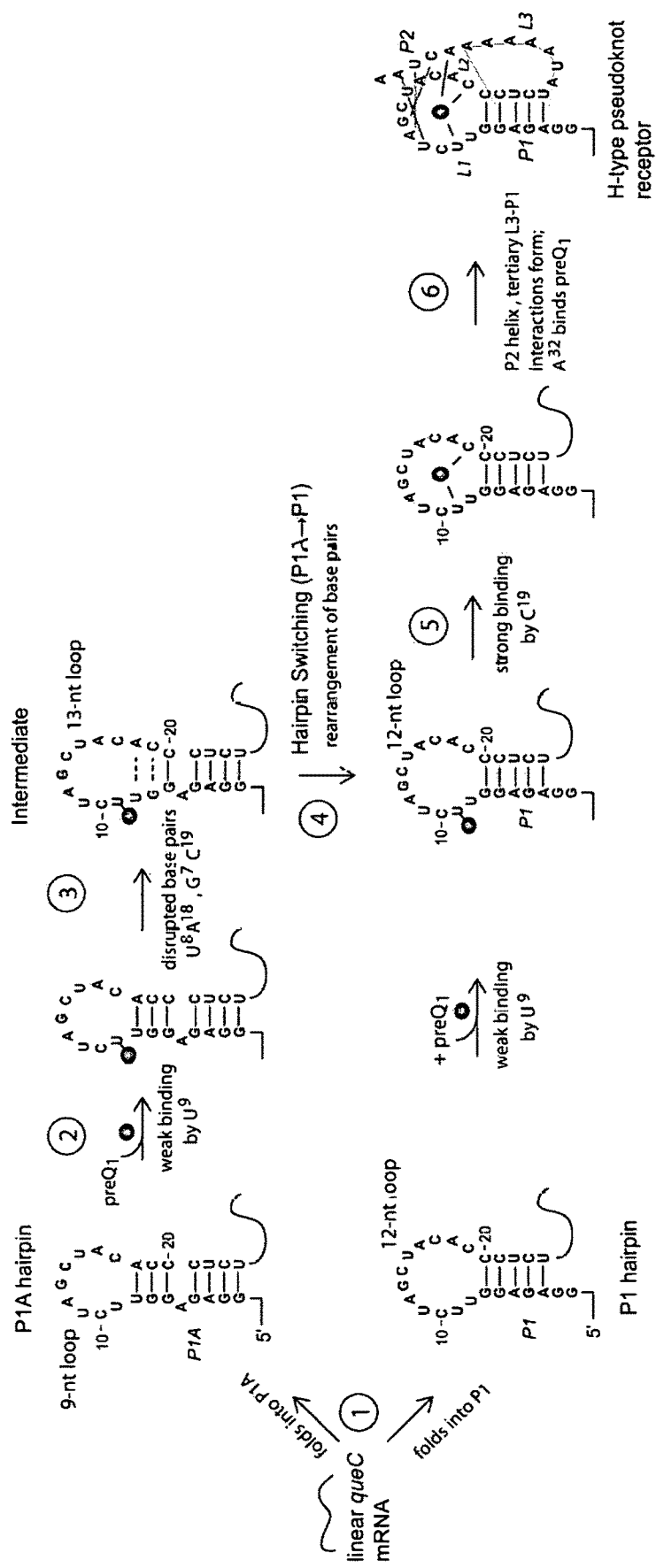
FIG. 5 is a schematic representation of the 33-nt H-type pseudoknot structure folding by hairpin switching. The folding of the pseudoknot follows a sequential pathway (steps 1-6) proceeding from the 5'→3' direction. The 24 nucleotides at the 5'-end of the queC mRNA can fold into either the P1A or P1 helical conformations. However, P1A cannot form the pseudoknot without first undergoing a structural rearrangement. The proposed scheme highlights a ligand-dependent hairpin switching mechanism that allows the P1A helix to fold into the H-type pseudoknot. The folding steps are: (1) formation of the initial hairpin at the 5'-end, (2) preQ$_1$ binds U9 (weak-binding), (3) formation of the intermediate, (4) hairpin switching P1A→P1, (5) formation of C$_{19}$-preQ$_1$-U$_9$ complex, (6) formation of tertiary L3-P1 interactions (shaded area), P2 helix (dashed lines). The binding of A$_{32}$ with C$_{19}$-preQ$_1$-U$_9$ complex concludes the H-type pseudoknot-receptor folding.
Figure 6:
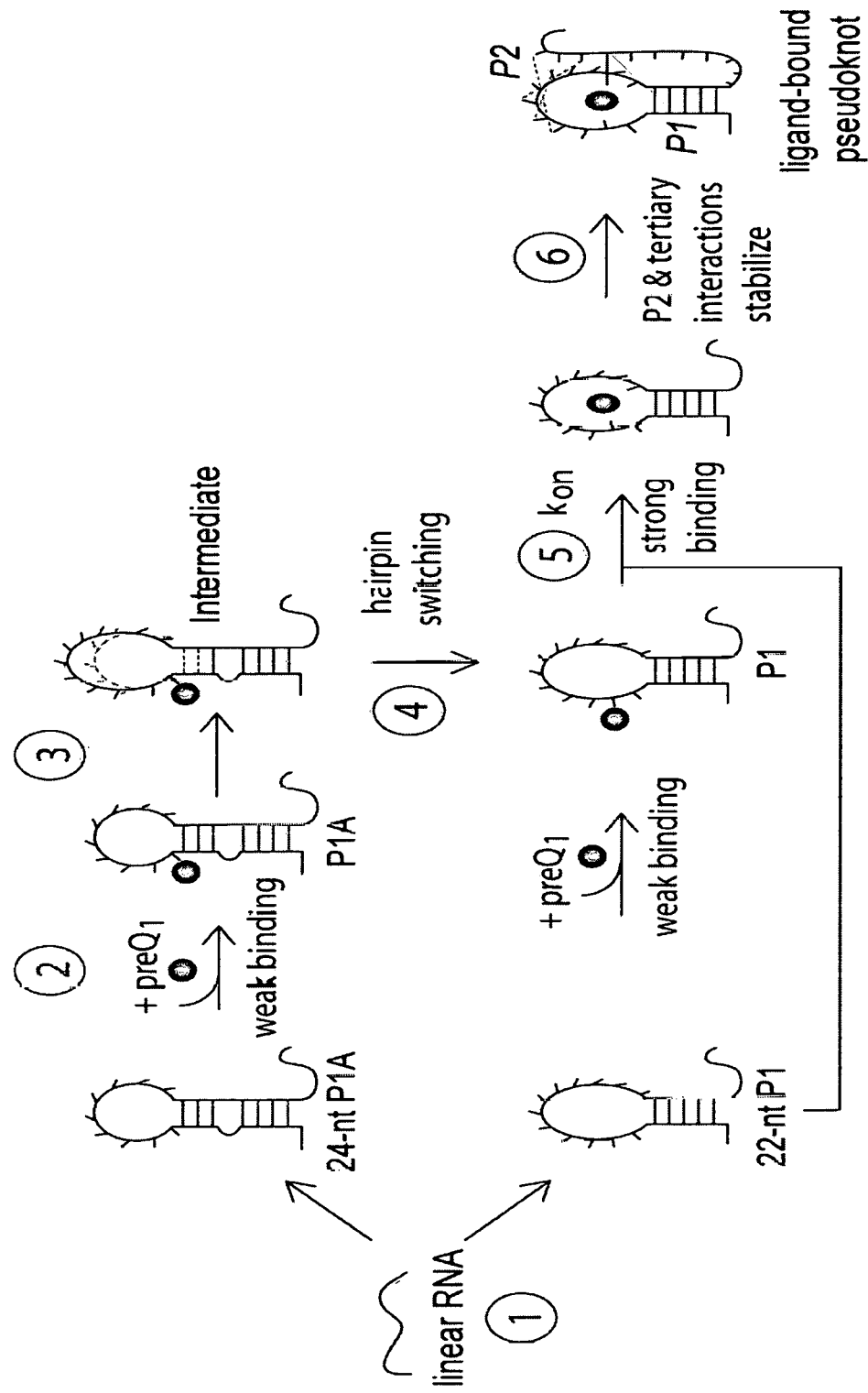
FIG. 6 is a schematic representation of the ligand induced hairpin switching (P1A→P1) to form the H-type pseudoknot structure. A six-step folding scheme for the H-type pseudoknot in the presence of preQ1 is depicted. AU, GC, and GU base-pairs are shown. Step 1—folding of the hairpin: the 5' sequence of the riboswitch RNA can fold into either the P1A or P1 conformations. Both the hairpins have competitive free energies; however, P1A is more favorable to form. Step 2—interaction with U9: once P1A folds, the nucleobase U9 interacts with the incoming ligand by forming one hydrogen bond. This results in weak-binding. Step 3—formation of intermediate: the binding of the preQ1 with U9 presumably causes a strain on the adjacent base pairs U8-A18 and G7-C19. This leads to the formation of the intermediate helix with a large apical loop. Step 4—hairpin switching: the intermediate conformation undergoes rearrangement in the base pairing sequence to form a shorter 5-bp P1 stem. This rearrangement is referred as P1A→P1 hairpin switching. The switching releases U8 and C19 nucleobases from base pairing interactions. A non-base paired U8 adjacent to the U9-preQ1 is favorable that stabilizes the binding pocket. Step 5—formation of ligand-receptor complex: the newly released C19 forms three hydrogen bonds with the preQ1 in an exothermic reaction (strong-binding) to form a ligand-receptor complex (U9-preQ1-C19). Step 6—formation of tertiary interactions: a series of tertiary AN6H interactions form between L3 and the newly formed P1-helix. Simultaneously, the base-pairing between C33G13, U34A12, A35U11 organizes the P2 helix. The tertiary interactions and the P2 helix is further stabilized by the hydrogen bonding between A32 and preQ1 to form the C19-preQ1-A32-U9 complex, which completes the pseudoknot receptor.

In CF traces, the 24-nt P1A hairpin that forms in the absence of ligand, and the 22-nt P1 helix, which is a part of the pseudoknot, displayed almost similar extensions (Table 1). Furthermore, they also displayed near similar kinetics within the error margin. Therefore, unless the ligand conditions were described alongside, it was challenging to distinguish between the two hairpins from the traces alone. The observations prompted the question, what if the linear mRNA indeed folds into P1A instead of P1, irrespective of the ligand? If so, will P1A then allow the formation of the pseudoknot structure? This is not an unlikely scenario, as P1A is more stable ($\Delta G=-0.7$ kcal/mol) than P1, hence more favorable to form. To explain this, a six-step folding scheme is proposed by which the incoming ligand induces a hairpin switching mechanism from P1A to P1 conformation (abbreviated as P1A→P1 hereafter) to form the pseudoknot. The complete mechanism is illustrated in FIG. 5.

According to the scheme, the 5' end of the riboswitch mRNA can fold into either the P1A or P1 helical conformation, which is discussed further below. In case P1A forms (step 1), the nucleobase $U_9$ initiates binding with the incoming ligand. Since $U_9$ can form one hydrogen bond with the preQ$_1$, the interaction is considered weak (FIG. 1). Nevertheless, the binding of preQ$_1$ destabilizes the adjacent $U_8$-$A_{18}$ and $G_7$-$C_{19}$ base pair interactions due to steric hindrance, forming the intermediate (step 3). The base-paired helical region in the intermediate rapidly undergoes a rearrangement to form a stable 5-bp stem, thus transforming the P1A helix into P1 (step 4). The newly formed base pairs are $G_7$-$C_{20}$, $G_6$-$C_{21}$ and $A_5$-$U_{22}$. The switching of the hairpin has distinctive advantages in the riboswitch mechanism of action: Foremost, it frees the residues $U_8$ and $C_{19}$ from base-pairing. This enables $C_{19}$ to interact with preQ$_1$ via multiple hydrogen-bonds (strong-binding in step 5). Secondly, a sequential binding ($U_9$ followed by $C_{19}$) facilitates the screening of the right ligand (specificity) into the binding pocket, whereby the initial weak-binding is reinforced by multiple H-bonds. This triggers the formation of the 3-bp P2 (step 6) and the tertiary interactions L3-P1, which stabilizes the binding pocket. The hydrogen bonding between $A_{32}$ and the $C_{19}$-preQ$_1$-$U_9$ complex concludes the formation of the H-type pseudoknot receptor.

By contrast, the folding is straightforward if P1 helix forms initially (step 1). Here, the incoming ligand can either bind sequentially ($U_9$ followed by $C_{19}$), or concurrently to form the pseudoknot structure. The structural rearrangements in the secondary and the tertiary interactions are driven by the exothermic binding, discussed later in FIG. 9.

Engineered Mutations Confirm Ligand-Induced Hairpin Switching

Figure 7:
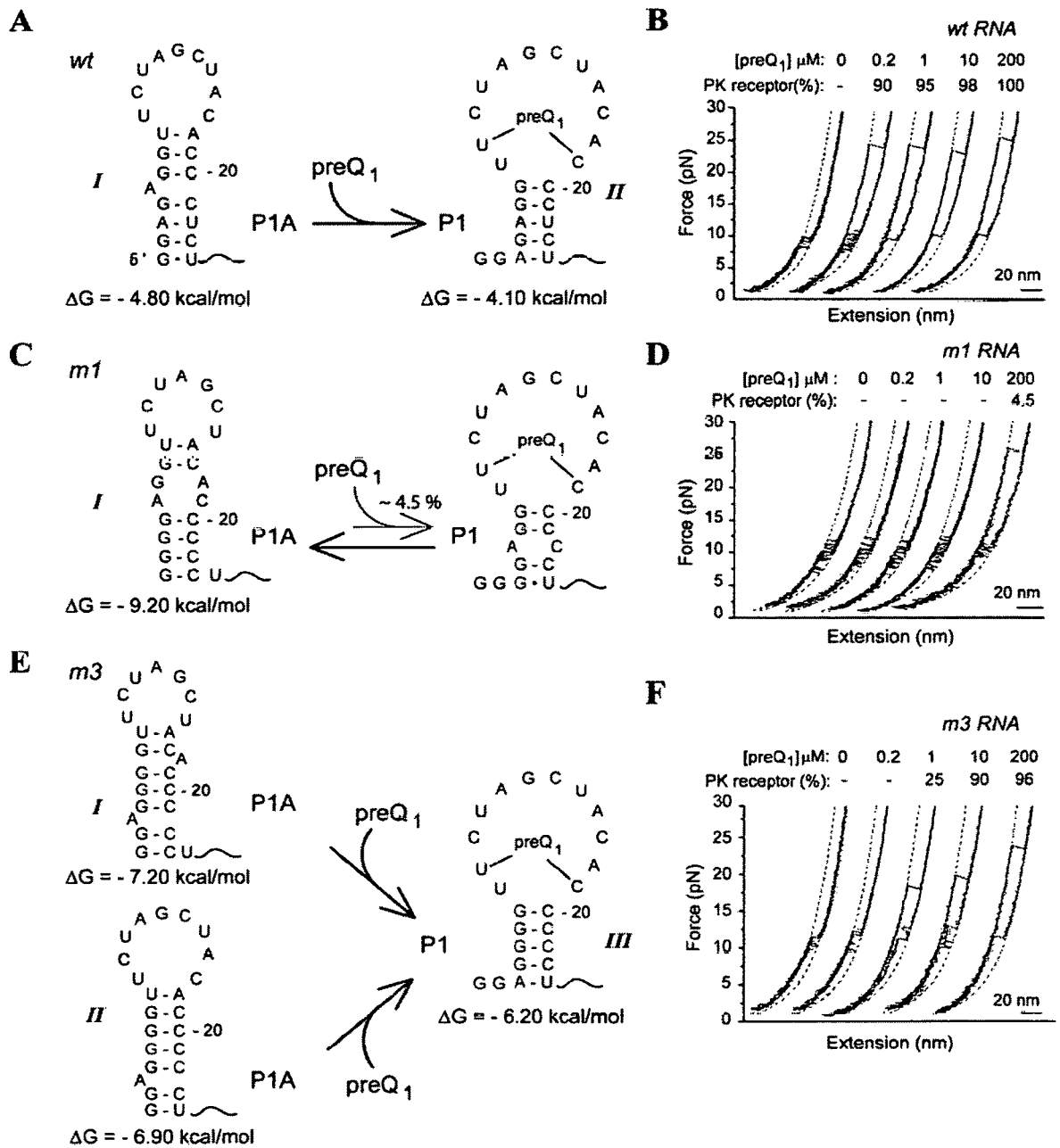
FIGS. 7A-7E illustrate the 5' hairpin undergoing switching to form the pseudoknot structure in the presence of a ligand.
FIG. 7F illustrates force extension curves (FECs) that indicate that the mutant (m3) RNA can form a pseudoknot structure at 1 µM preQ$_1$.

The proposed P1A→P1 hairpin switching mechanism was assessed by site-directed mutational strategies followed by mechanical assays. Essentially, the switching mechanism has two directed purpose—i) releasing $C_{19}$ from base pairing interactions, and ii) rearrangement of the base pairs in P1A to form the P1 helix. According to the M-fold prediction, the 24 nucleobases at the 5'-termini of the wild-type (wt) queC mRNA can fold into either I or II helical conformations (FIG. 7A). The competitive free energies indicate that the two conformers coexist in equilibrium (I↔II). While conformer I resembled P1A, conformer II can be related to the P1 structure, which is a part of the pseudoknot. From the mechanical assays, it was found that the addition of 0.2 µM preQ$_1$ in the buffer is sufficient to tilt the hairpin equilibrium toward the pseudoknot structure. In fact, ~90% of the traces (109 out of 120 traces) displayed the characteristic pseudoknot signature in the force-extension curves (FIG. 7B). This suggested that the 5'-sequence of the riboswitch indeed plays a crucial role in directing the folding events toward the pseudoknot conformation.

To further test this, mutations were incorporated in the 5' end of the riboswitch, while the remaining sequence was kept intact. Thus, in the mutant (m1) RNA, the residues A3 and U22 were replaced with G3 and C22 respectively (FIG. 7C). Specifically, the modifications stabilized the lower portion of the helix stem, while the upper region incorporated the bulge due to mismatches. Thus, it was verified that the binding abilities of $C_{19}$ with preQ$_1$ are unaffected, while restricting the structural rearrangements in the helix required for the pseudoknot formation. The altered sequence resulted in a stable hairpin structure ($\Delta G=-9.20$ kcal/mol). As expected, the mutant (m1) RNA construct was severely disabled to form the pseudoknot structure, despite high preQ$_1$. A significantly low 4.5% of traces (11 out of 242 traces) exhibited the pseudoknot conformation only at saturating 200 µM preQ$_1$ (FIG. 7D). The results thus underscore that the $C_{19}$-preQ$_1$ binding must be followed by the base pair rearrangement for a successful hairpin switching, which can then lead to the H-type pseudoknot receptor conformation.

Figure 8:
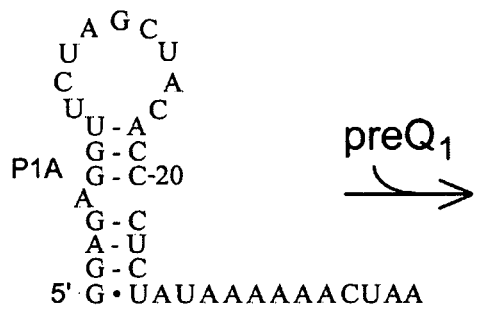
FIGS. 8A-8C illustrate the complete sequence and the secondary structures for the wt RNA and two mutants (m1) and (m3) in the absence and the presence of preQ1. The dashed lines indicate P2 base-pairing. The A-rich L3 interacts extensively with the P1 through a series of AN6H hydrogen bonds via the minor groove (shaded bases and the grey lines). For comparison, the tertiary interactions are shown for the wt RNA and the m3 mutant.
Figure 8:
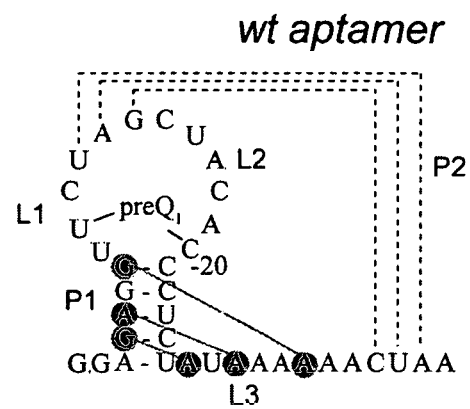
Figure 8:
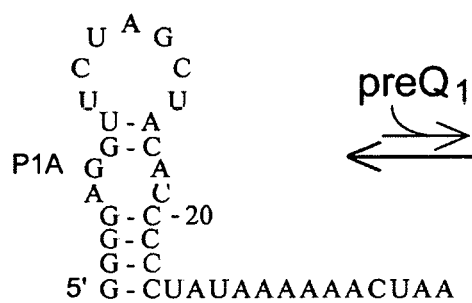
Figure 8:
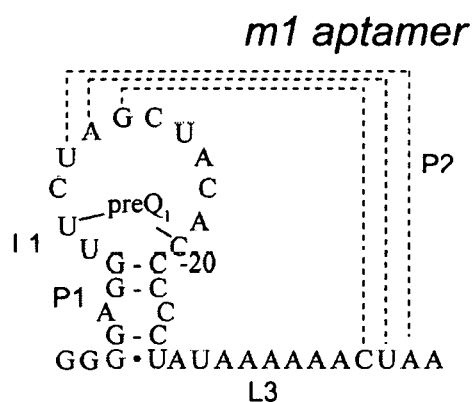
Figure 8:
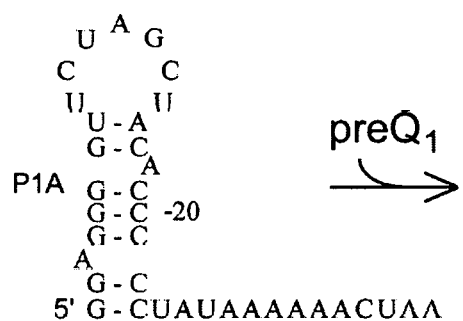
Figure 8:
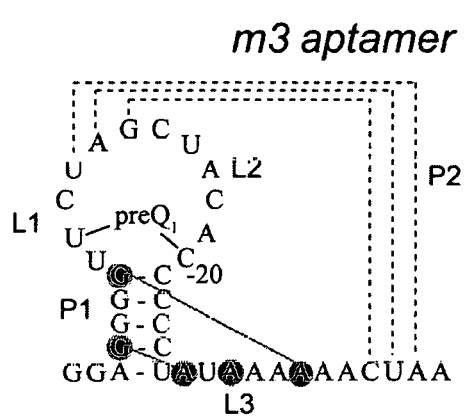
Figure 9:
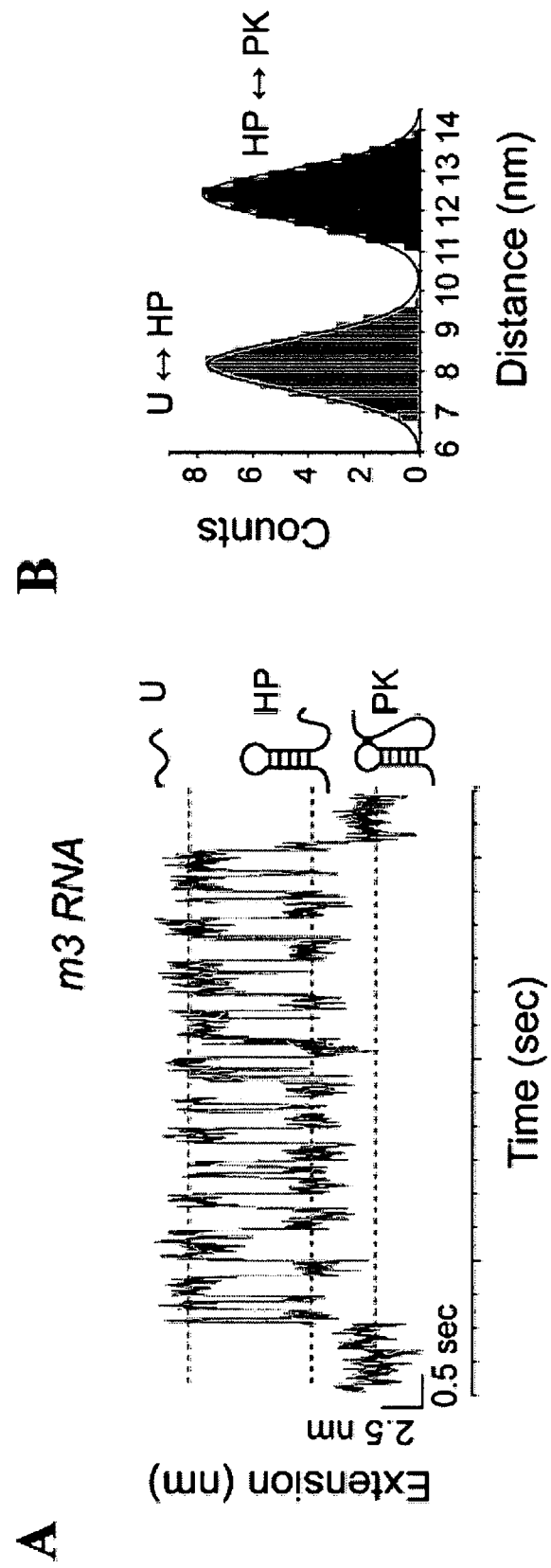
FIGS. 9A and 9B illustrate that a mutant (m3) RNA fluctuates between three conformational states at 12 pN.

A mutant (m3) RNA was also designed by substituting A5, U22 with G5, C22 residues (FIG. 7E). According to the M-fold, the mutant (m3) RNA can fold into any of the three conformations—I, II or III. All the conformers exhibited competitive free energies as indicated in FIG. 7E. A comparison of the average free energies favored the m3 mutant ($\Delta G_{av.}=-6.8$ kcal/mol) than the wt ($\Delta G_{av.}=-4.45$ kcal/mol). The FECs in FIG. 7F show that the pseudoknot conformation was restored in m3, although at 1 µM preQ$_1$. Evidently, 25% of the traces (28 out of 113 traces) displayed the pseudoknot structure. This may be due to the modified sequence that rendered a weak L3-P1 tertiary interaction (FIG. 8), thereby affecting the pseudoknot stability. Additionally, the m3 RNA exhibited the three-state fluctuation (U↔HP↔PK) in the presence of preQ$_1$ (FIG. 9). The equilibrium $F^{eq}$ was observed at 12 pN. Taken together, the mutants convincingly support the proposed scheme in FIG. 5, whereby the initial ligand-binding triggers a unidirectional P1A→P1 hairpin switching, which is the key for the H-type pseudoknot receptor conformation.

Thermodynamics and the Free Energy Landscape During Pseudoknot Formation

Figure 10:
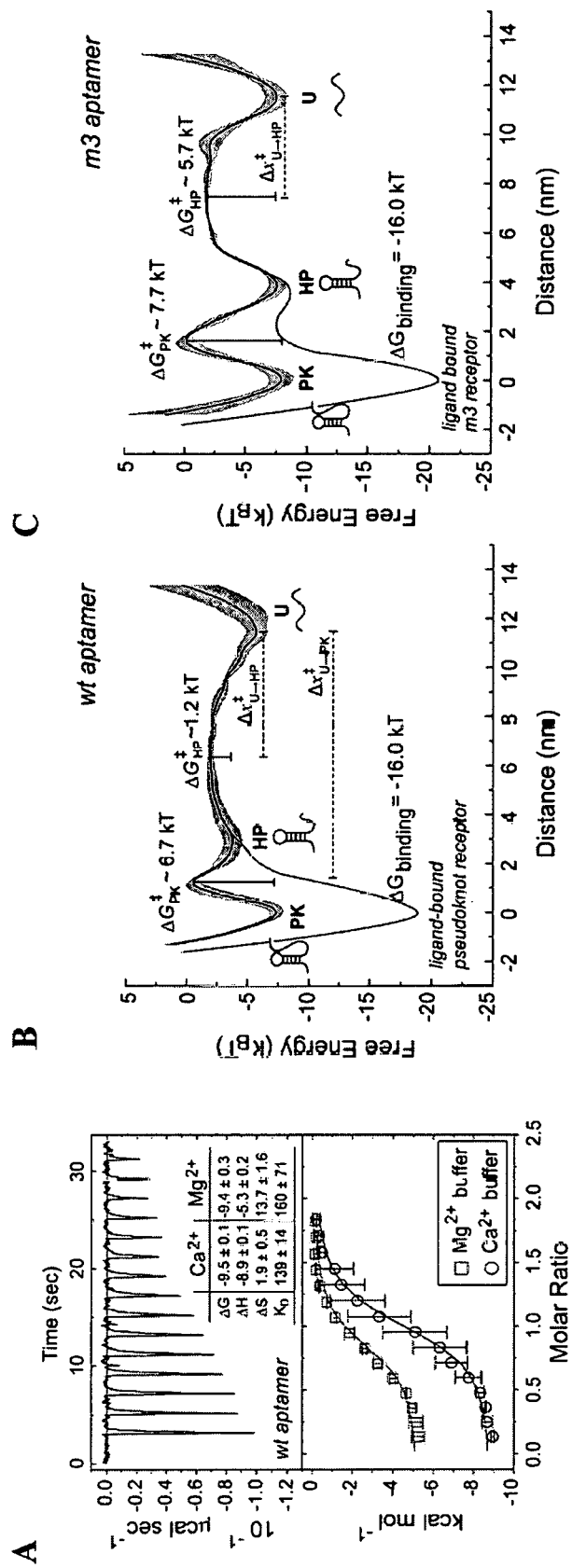
FIGS. 10A-10C illustrate the free energy landscape highlights between two barriers in the pseudoknot folding.

Next, to assess the thermodynamic parameters in preQ$_1$-dependent pseudoknot structure, isothermal titration calorimetry (ITC) was performed. The RNA backbone being negatively charged requires counterions for folding, hence two separate buffer systems, $Mg^{2+}$ and $Ca^{2+}$ buffers for the titration experiments were used. The calorimetric data indicated an exothermic reaction (FIG. 10A). Apparently, the net enthalpic change ($\Delta H$) for the ligand-receptor binding interaction is more favorable in $Ca^{2+}$ buffer ($-8.9\pm0.1$ kcal/mol) than the $Mg^{2+}$ buffer ($-5.3\pm0.2$ kcal/mol). This also suggests that the affinity of the queC RNA for the metal ion $Ca^{2+}$ is stronger compared to $Mg^{2+}$. Experimental and simulation studies have also indicated that the affinities for divalent ions for DNA strands decreases in the order $Ca^{2+}>Mg^{2+}>>Na^+\approx K^+$. Nevertheless, the net free energy change, $\Delta G_{binding}=-9.5\pm0.1$ kcal/mol (or $-16.0\pm0.2$ kT) remained unaffected by the type of divalent ions in the buffer. This could be mainly because, in the $Mg^{2+}$ containing buffer, a high positive entropy ($\Delta S=13.7\pm1.6$ cal/mol/deg) is balanced by low enthalpic change (FIG. 9A, inset). Then, according to the relation $\Delta G=\Delta H-T\Delta S$, the overall free energy is favorable enough to drive the folding reaction toward the pseudoknot conformation.

Finally, the free energy landscape was reconstructed for the transition of the linear RNA chain to the H-type pseudoknot receptor. A complete free energy landscape with well-defined barrier properties, such as the transition distances ($\Delta x^\ddagger$) and the barrier heights ($\Delta G^\ddagger$), provides unparalleled insights into the folding reaction. Briefly, to plot the free energy landscape, the actual RNA extensions were first extracted by following a deconvolution procedure described previously. In single molecule experiments, accurate deconvolution is important as the molecular extensions are often masked by the thermal noise from the beads and the handles (see FIG. 2B). Thereafter, the Boltzmann relation, $\Delta G(x, F) = -k_B T \ln(P(x, F))$, where $P(x,F)$ is the extension probability density at the given force, F, was used to plot the complete free energy landscape along the end-to-end unfolding distance. The free energy landscape for the wt riboswitch molecule is shown in FIG. 10B. Furthermore, to increase the confidence level of the free energy landscape, fluctuations were measured at three different forces (10 pN, 9.5 pN, and 9 pN). All three forces varied within the narrow range (±0.5 pN) from the equilibrium. The solid black curve represents the average free energy. The estimated std. dev. ~1 kT is indicated by the shaded area. The plot underscores that the nascent RNA encounters two barriers en route to the native pseudoknot receptor. The first barrier at $\Delta x^\ddagger_{U \to HP} \sim 5.5$ nm is located prior to the formation of the hairpin (U→HP). The low barrier height, $\Delta G^\ddagger_{HP} \sim 1.2$ kT (or 0.7 kcal/mol) suggests that the hairpin folding largely proceeds uninterrupted. It is reminded that the two competing helices, P1 and P1A, differed in their free energies by 0.7 kcal/mol, according to the M-fold prediction. This underscores that the single-molecule approaches to determine barrier properties agree with the theoretical values within the error limits.

Interestingly, the plot also indicated that subsequent folding to form the pseudoknot receptor (HP→PK) is not straightforward. The nascent RNA encounters a second barrier prior to the pseudoknot folding at the transition distance, $\Delta x^\ddagger_{U \to PK} \sim 10$ nm. The observed barrier height, $\Delta G^\ddagger_{PK} \sim 6.7$ kT (or 4.0 kcal/mol) is 6-fold steeper than $\Delta G^\ddagger_{HP}$, suggesting that the folding of the nascent RNA beyond the hairpin state is stalled in the absence of the ligand. However, the exothermic ligand-binding ($\Delta G_{binding} = -16$ kT) presumably facilitated the barrier crossing (FIG. 10B). Evidently, by coupling the exothermic binding with the folding events, the nascent RNA ensures the formation of the native pseudoknot receptor. The accuracy of the barrier positions was also assessed by using the Bell's relation, $$k = k_0 \exp\frac{F \Delta x^\ddagger}{k_B T},$$

where $k_0$ is the intrinsic rate, $k_B$ the Boltzmann constant, and T temperature. The calculated transition distances indicated in Table 1 overlapped with the barrier positions highlighted by the peaks in the free energy landscape.

Similarly, the free energy landscape was reconstructed for the mutant (m3) RNA at 11.5 pN, 12.0 pN, and 12.5 pN, shown in FIG. 10C. The plot highlights that the nucleobase substitutions significantly increased the hairpin barrier ($\Delta G^\ddagger_{HP}$) to 5.7 kT in m3 from 1.2 kT in the wt RNA. The $\Delta G^\ddagger_{PK}$ also increased marginally by ~1 kT. This necessitated higher preQ$_1$ concentrations to induce the hairpin switching required for the pseudoknot conformation.

Discussion

Here, the 36-nt queC preQ$_1$-riboswitch from *B. subtilis* was employed to investigate the folding pathways, kinetics, thermodynamics and the free energy landscape in the formation of the H-type pseudoknot using single-molecule mechanical experiments. Two modes of force application were used—constant-speed (CS) and constant-force (CF). The non-equilibrium CS measurements allowed the quantification of the bound-receptor conformation at different ligand conditions. Thus, in the absence or low preQ$_1$, the FECs indicated a hairpin structure similar to the 24-nt P1A (FIGS. 2B, 2C). In the presence of 0.2 μM or higher preQ$_1$ concentrations, the mechanical traces indicated a distinct transition, which corresponded to the 33-nt H-type pseudoknot structure. On the other hand, the equilibrium data by CF measurements revealed that the pseudoknot folding is directional, which proceeds from the 5'→3' end of the transcript. Furthermore, at equilibrium the extension population densities suggested that the linear mRNA folds into the H-type pseudoknot via an intermediate hairpin state. It is shown herein that in the presence of the right ligand, the hairpin undergoes a conformational switching from P1A→P1, which in turn triggered the structural rearrangements in the secondary and the tertiary interactions to form the binding pocket, thereby enabling the 3' tail to fold into the pseudoknotted conformation. In other words, the P1A→P1 hairpin switching is the key to the preQ$_1$-assisted pseudoknot formation. The complete folding scheme is illustrated in FIG. 5.

The hairpin switching mechanism was assessed by incorporating mutations in the riboswitch 5' end. The data indicated that overall the 5'-sequence in the preQ$_1$ riboswitch plays a deterministic role in the pseudoknot formation. The m1 mutant RNA, which formed a very stable P1A helix, resisted any P1A→P1 hairpin switching (FIG. 7), thereby resulting in a substantially low pseudoknot population (~4.5%) even at high 200 μM preQ$_1$. On the contrary, the m3 mutant RNA with moderately stable P1A helix restored the hairpin switching phenotype, and the pseudoknot formation. In the mechanical assay, the pseudoknot conformation was detected in 25% of traces at 1 μM preQ$_1$. By comparison, 90% of the traces in the wt RNA displayed the pseudoknot conformation at a low 0.2 μM preQ$_1$. Evidently, this underscores that the hairpin switching is crucial for the pseudoknotted structure.

Additionally, the free energy landscape (FIGS. 10B, 10C) along the folding reaction coordinate, $\Delta G(x,F)$ revealed that the conversion of the linear RNA to the pseudoknot structure is not straightforward, rather interrupted by two kinetic barriers. In the wt construct, the first barrier ($\Delta G^\ddagger_{HP} \sim 1.2$ kT) is located at the hairpin, which is relatively low than the second barrier height, $\Delta G^\ddagger_{PK} \sim 6.7$ kT. This implied that a successful barrier crossing could take place only in the presence of preQ$_1$. This is mainly because, as preQ$_1$ binding is exothermic (−16 kT), the riboswitch can harness the binding-energy to cross the barriers. In fact, in the absence of preQ$_1$, the barrier crossing and the switching of the hairpins were stalled in the wt RNA and the mutant RNAs m1 and m3. In the mutant (m3) RNA, the first barrier height at the hairpin was engineered to be steep ($\Delta G^\ddagger \sim 5.7$ kT) due to the mutations. Consequently, the efficiency of hairpin switching (P1A→P1) reduced. In other words, the hairpin switching could be restored only upon further addition of ligand at 1 µM. This highlighted that the combination of the hairpin sequence and the ligand is necessary to induce hairpin switching, that is necessary for the pseudoknot receptor structure. It is anticipated that the findings and the strategies presented herein will be extended toward deciphering the folding pathways and the assembly of other RNA structures that perform regulatory functions in the cell.

Methods

Synthesis of queC and Mutant RNA Constructs for Single-Molecule Experiments

The 36-nt wild-type (wt) queC RNA from *B. subtilis* and the mutant constructs m1 and m3 were generated as following. First, the DNA sequence was synthesized as an EcoR1-HindIII fragment. The product was cloned into a pBR322 vector following standard molecular biology protocols. The integrity of the insert was assessed by cleavage with ClaI-TaqI restriction enzymes that generated a 250 bp DNA fragment on agarose gel electrophoresis. The product was purified and the sequence confirmed by DNA sequencing (Genewiz Inc.). Next, a 1.1 kB long DNA fragment was PCR amplified from the cloned vector using the primers shown below. The following underlined bases represent the T7 promoter sequence.

5'-
TAATACGACTCACTATAGGGACTGGTGAGTACTCAACCAAGTCATTCTG
and

5'-TAGGAAGCAGCCCAGTAGTAGGTTGAGGCC

The DNA fragment was amplified by polymerase chain reaction (PCR) comprising the insert and the flanking sequences at each end. The PCR product (1.1 kB dsDNA) was purified to remove unincorporated primers, free dNTPs, and transcribed in vitro using T7 Ribomax kit (Promega). The flanking sequences viz., Handle A (533 bp) and Handle B (599 bp) were separately PCR amplified. Handle A was chemically modified to incorporate digoxigenin-11-dUTP (Roche Diagnostics) by Klenow fill-in reaction. Handle B was labeled with 5'-biotin using a modified primer sequence. All primers were obtained from Integrated DNA Technology (IDT Inc.).

For single-molecule experiments in our optical-tweezer, the dsDNA handles and the transcript was annealed in a buffer. The assembled DNA Handles-RNA transcript (DNA-RNA hybrid) was ethanol precipitated and reconstituted in aqueous buffer containing 10 mM Tris, pH 7.5 at 23° C., 250 mM NaCl, and 3 mM $MgCl_2$. All single-molecule experiments were performed in the above buffer, with or without the ligands as indicated in the text.

Establishing Single-Molecule Connection in Optical Tweezers

In custom-built counter-propagating dual-beam optical tweezers (λ, 845 nm), one nanometer distance change at sub-picoNewton forces (±0.15 pN) with a time resolution of 25 µsec can be measured. The instrumental details and resolution have been described previously. In a typical experimental set up, the larger anti-digoxigenin (Adig) coated beads with diameter 4.0-4.9 pm (Spherotech Inc.) was trapped in the lasers, while the streptavidin (SA) coated bead with diameter 1.5-2.5 µm (Spherotech Inc.) was held on the micropipette via suction. Both beads were connected by a single-molecule connectivity, as shown schematically in FIG. 2A. To establish a single molecule connection, the following procedure was used. At first, the DNA-RNA hybrid mixture was diluted appropriately in the buffer (10 mM Tris, 250 mM NaCl, and 3 mM $MgCl_2$). The diluted mixture was then incubated with the Adig beads at room temperature for 15 minutes to facilitate digoxigenin-anti-digoxigenin interaction.

Next, the Adig beads with attached molecules were flown into the microchamber, wherein one bead was trapped in the laser beams. The trapped Adig bead was then moved closer to the SA bead, held on the micropipette. At close vicinity, the free end of the Handles (containing biotin) established connections with the SA bead through streptavidin-biotin interaction. That the bead pair is connected by a single-molecule was further assessed by the following methods: a) fitting the force-extension curves with a serial WLC model (Eq. 1); b) measuring the overstretch transition, and c) measuring the rupture force on a graphical user interface (GUI). A single-molecule connection typically displayed WLC fitted force-extension curves with overstretch transition around 63-65 pN.

In the above procedure, the initial dilution of DNA-RNA mixture is critical to ensure fewer molecules on the surface of the beads. This in turn increased the likelihood of one tether between the bead pair. On the other hand, a non-diluted mixture resulted in densely distributed RNA molecules on the bead surface that eventually formed multiple connectivities between beads. Such connections could not be fitted by a serial WLC equation, and often the rupture forces exceeded more than 90 pN. Once a single molecule connectivity was established, experiments were conducted in constant-speed (CS) or constant-force (CF) mode, as described below.

Mechanical Folding Assay: Constant-Speed (CS) and Constant-Force (CF) Experiments A calibrated force was employed to follow the pseudoknot formation in the queC mRNA. Toward this end, two kinds of mechanical folding experiments were performed, constant-speed (CS) and constant-force (CF) as described previously.

Briefly, in the CS experiment, a tethered riboswitch molecule was stretched and relaxed between 1 pN and 30 pN. The pulling speed was constant at 200 nm/s that corresponded to a loading rate of 7.6 pN/s. The CS experiments were sampled at 400 Hz. The data is plotted as force vs. extension curves (FECs) without any smoothing as in FIG. 2C. All FECs were fitted with the WLC equation (Eq. 1) for further analysis. In the constant-force (CF) assay, the RNA was held at a preset force, wherein the molecule fluctuated between the various conformational states namely, linear (U), hairpin (HP) and pseudoknot (PK) structure. The preset force typically fluctuated around the mean ±SD (±0.15 pN). The preset force was maintained through a feedback control loop. To record both the fast and slow kinetics, a 4000 Hz sampling rate was used. Data from CF experiments are shown as extension versus time traces, and filtered by a 300-point moving average (FIG. 4A).

Data Analysis

Sample Size and Statistics

The results from force-extension measurements (CS assay) are indicated as ±SEM by pulling at least 10 or more independent molecules in the ligand concentrations. Each molecule was subjected to multiple rounds of stretch-relax cycles at the loading rate, 7.6 pN/s. All transition forces, and distances exhibited a Gaussian distribution as shown in FIGS. 2D and 2E. The mean values are indicated in Table 2 below.

The kinetic rates for the wt and mutant m3 RNAs were determined by analyzing at least 20 or more traces, as indicated in Table 1 below. The free energy landscapes for the wt RNA and the mutant (m3) RNA in FIGS. 10B and 10C were measured at three forces. The isothermal calorimetry (ITC) experiments are shown as average from three independent experiments. All statistical uncertainties associated with the reported mean values are represented as SEM or SD, as the case may be.

WLC Fit to Force-Extension Curves (FECs)

The FECs obtained from the CS experiments were fitted to the modified Marko-Siggia worm-like-chain (WLC) equation:

$$F_{WLC}(x) = \frac{k_B T}{P}\left[\frac{1}{4}\left(1 - \frac{x}{L} + \frac{F}{K}\right)^{-2} - \frac{1}{4} + \frac{x}{L} - \frac{F}{K}\right] \quad \text{(Eq. 1)}$$

where $k_B$ is the Boltzmann's constant and 1 $k_B T$=4.057 pN·nm at 294 K, x is the extension, P is the persistence length, L is the contour length, and K is the stretch modulus. The unfolding and the refolding traces were individually fitted based on the parameters: $P_{handle}$=2~3 nm, $L_{handle}$=0.25 nm/bp, $K_{handle}$=500~800 pN, $P_{RNA}$=1 nm, $L_{RNA}$=0.59 nm/base, $K_{RNA}$=1600 pN. The persistence length and the stretch modulus fitted well to the previously described values.

Determination of Probability of Bound-Receptor, P(F$_u$)

The probability of the bound-receptor conformation was determined from the FECs. Typically, the bound-receptor conformation showed the characteristic unfolding near ~22 pN with a rupture distance ~16 nm that corresponded to ~33 nts pseudoknot structure. Considering that a tethered RNA has equal likelihood to adopt a bound or unbound conformation, a higher probability (≥90%) implied that the mRNA exhibited pseudoknot structure in consecutive traces. For instance, out of 187 FECs recorded for the wt aptamer in 10 µM preQ$_1$, 184 traces displayed the characteristic pseudoknot unfolding signature as described above. Such transitions were referred as 'bound-trajectories'. Thus, P(bound-receptor)=98.4% (wt) during unfold (F$_u$) cycle, as indicated in FIG. 2F. The SEM was then calculated by the formula, $$\sigma_P = \sqrt{\frac{P(1-P)}{N}},$$

where N is the total number of traces and P the bound-conformation.

Identification of States

For the sequential folding along U→HP→PK, the observed extensions between the states were discrete. Therefore, a two-state analysis based on the threshold method to identify transition between any two states was used. The states and the conversion rates were also assessed using the QuB software, which uses the Hidden Markov Model (HMM) to infer states with maximum likelihood, as shown previously for single-molecule studies.

Determination of Kinetic Rates

The folding ($k_f$) and the unfolding ($k_u$) kinetic rates between two states was determined from the extension versus time traces recorded in CF experiments. At a given force, if a molecule hopped between the folded (F) and the unfolded (U) state, then the time spent at any given state, referred as the dwell time (τ), is proportional to the inverse of the rate constant (k). Therefore, if the transition occurred from folded→unfolded state, then the rate of unfolding ($k_u$) is inversely dependent on the amount of total time spent at the folded state ($τ_f$) before the molecule transitioned to the linear form. Mathematically, the unfolding rate constant ($k_u$) is then expressed as:

$$k_u = \frac{1}{\langle \tau_f \rangle} \quad \text{(Eq. 2)}$$

Similarly, the folding rate ($k_f$) from U→F can be written as:

$$k_f = \frac{1}{\langle \tau_u \rangle} \quad \text{(Eq. 3)}$$

where, $\langle \tau_f \rangle$ and $\langle \tau_u \rangle$ are the average durations measured from multiple traces.

Determination of Transition Distances (Δx$^{\ddagger}$)

In the mechanical folding assays, the kinetic rates are dependent on the applied force. Therefore, the force-dependent rate constants, $k_u$(F) during unfolding (F→U) can be described by the Bell's equation as, $$k_u(F) = k_0 \exp\frac{F\Delta x^{\ddagger}}{k_B T} \quad \text{(Eq. 4)}$$

where $\Delta x^{\ddagger}_u$ is the distance to the transition state from the folded conformation, and $k_0$ is the intrinsic rate in the absence of force. The calculated $\Delta x^{\ddagger}_f$ and $\Delta x^{\ddagger}_u$ for the folding and unfolding pathways are indicated in Table 1. The transition distances overlapped with the peaks in the free energy landscapes in FIGS. 10B and 10C indicating a complete agreement of the two methods.

Deconvolution Procedure and the Free Energy Landscape

For equilibrium assays, the actual RNA extensions are often blurred by the thermal motions of the beads and handles. Therefore, to recover the actual extensions, the experimental probability distribution P$^0$(x) is deconvoluted with a point spread function, PSF(x) that represents the fluctuations due to thermal noise. To determine the latter, a molecular construct (as control) was designed with 7-nt single-stranded RNA and hybridized it with the handles. The control was then subjected to the CF experiments under similar instrumental settings as the wt preQ$_1$ riboswitch. The PSF(x) obtained from the construct was fitted by the Gaussian distribution and used for deconvolution procedure. A non-linear constrained iterative method as described earlier in the mechanical studies was used. Briefly, the probability distribution at the (k+1)th iteration was determined by using the relationship, $$P^{k+1}(x)=P^k(x)+r(P^k(x))\times[P^0(x)-\text{PSF}(x)\otimes P^k(x)];$$

$$r(P^k(x))=r_0(1-2|P^k(x)-\tfrac{1}{2}|), \quad \text{(Eq.5)}$$

where $\otimes$ denoted the convolution operator, and $r(P^k(x))$ represented the relaxation function, which constrained the solution to remain within the physical boundary $0 \leq P^k(x) \leq 1$. Starting with the measured probability distribution $P^0(x)$, $r_0=1$ with $n \approx 8000$ iterations was used. To reduce artifacts introduced by the discrete convolution computation, the extension distribution and PSF(x) were sampled within a 0.02 nm interval. Besides, both the initial distribution $P^0(x)$ and the final solution $P^n(x)$ were smoothed by a 0.5 nm moving average. Finally, to test the accuracy of the deconvolution procedure, the residual error was determined by the formula, $$R(x)=P^0(x)-\text{PSF}(x)\otimes P^n(x) \quad \text{(Eq.6)}$$

Once the final solution $P^n(x)$ was reached, the associated landscape $\Delta G^n(x)$ was calculated following the Boltzmann relation (Eq. 7). The relation was used to plot the free energy landscape, $\Delta G(x)$ for both the wt RNA and the mutant (m3) RNA along the end-to-end distance of the respective molecules.

$$\Delta G(x, F)=-k_B T \ln(P(x, F)) \quad \text{(Eq.7)}$$

where, P(x) is the extension probability distribution measured at a given force, F. The free energy landscape for the wt RNA and the mutant (m3) RNA was reconstructed at three different forces within a narrow range (±0.5 pN). The estimated SD was ~1kT. The average free energy landscape is shown in FIGS. 10B and 10C.

Isothermal Titration Calorimetry

Isothermal titration calorimetry (ITC) experiments were performed to determine the thermodynamic parameters ($\Delta G$, $\Delta H$, $\Delta S$) for preQ$_1$ binding to the 36-nt queC aptamer. The required RNA construct was synthesized by in-vitro transcription. The product was purified by 20% denaturing polyacrylamide gel electrophoresis. Binding experiments were performed at 30° C. on a MicroCal iTC200 instrument (Malvern). The instrument was set at the reference power 6 µcal/s, with initial delay 60 s, and a stirring speed 750 rpm. The titration experiments were performed as described below. The RNA was suspended in the cell with concentrations ranging from 5-15 µM, while the syringe contained the ligand preQ$_1$. The ligand concentration was 9-10 fold higher than the RNA. Both ligand and RNA was reconstituted in the same buffer to avoid mixing enthalpy. PreQ$_1$ was titrated into the sample cell in 16 injections (2.5 µl each). The injection rate was 0.5 µl/s, with spacing between the injections maintained at 120 s. Data was baseline corrected and fitted to a single site binding model to obtain the association constant ($K_A$) and binding enthalpy ($\Delta H$). The free energy change ($\Delta G_{binding}$) was obtained by using Eq. 8 and Eq. 9. Data was analyzed using the Origin software.

$$K_D=1/K_A \quad \text{(Eq. 8)}$$

$$\Delta G=RT \ln K_D=\Delta H-T\Delta S \quad \text{(Eq. 9)}$$

Specifically, in this study two buffer systems were used with different divalent concentrations ($Mg^{2+}$ and $Ca^{2+}$) to determine the effect on the binding isotherms for preQ$_1$. The composition for $Mg^{2+}$ buffer was 50 mM K$^+$ Hepes, pH 7.5, 100 mM KCl, and 20 mM MgCl$_2$, while the $Ca^{2+}$ supplemented buffer included 50 mM K$^+$ Hepes, pH 7.5, 100 mM KCl, 20 mM MgCl$_2$, and 50 mM CaCl$_2$. As shown in FIG. 10A, the binding enthalpy ($\Delta H_{binding}$) was influenced by divalent salt concentrations, however, the total free energy change ($\Delta G_{binding}$) remained constant irrespective of the buffer. The mutant (m3) RNA showed free energy similar to the wt RNA, indicating that the mutation did not affect the binding energies. The mutant (m1) RNA exhibited 4.5% pseudoknot conformation at 200 µM preQ$_1$, suggesting that the RNA has very low affinity for preQ$_1$, probably with $K_D$ values at millimolar range. For such low affinity interactions, a proper baseline could not be recorded, even after multiple (>10) trials.

Switching Speed and/or Switching Intensity

The speed in which a pseudoknot can switch between conformations in the presence of a ligand can be controlled by altering the wild type RNA structure. Stated another way, certain mutations to the wild type RNA structure cause the pseudoknot to form, or switch, slower than the wild type RNA while other mutations cause the pseudoknot to form, or switch, faster than the wild type RNA. The mutant (m1) RNA resisted the switching intensity as compared to the wild type RNA. In at least one instance, the mutant (m1) RNA exhibited 4.5% pseudoknot conformation as compared to the wild type RNA which exhibited 100% pseudoknot conformation in the presence of thousand-fold less preQ$_1$ concentration. The force applied to the RNA structure can also affect the speed in which the pseudoknot forms, or switches. Thus, the switching of the hairpin into a pseudoknot conformation is dependent on three factors—the ligand, the RNA sequence, and the applied force.

TABLE 1

Kinetics and transition distances ($\Delta x^{\ddagger}$) during folding (U→HP→PK) and unfolding (PK→HP→U) pathway

| [preQ$_1$] (µM) | Transitions | Distances $\Delta X$ (nm)[a] | Folding rate $k_f$ (s$^{-1}$)[b] | Unfolding rate $k_u$ (s$^{-1}$)[b] | Transition distance $\Delta x^{\ddagger}_{(U \to PK)}$[c] (nm) | Transition distance $\Delta x^{\ddagger}_{(PK \to U)}$[c] (nm) | $F^{eq}$ (pN)[d] | Number of traces (n) |
|---|---|---|---|---|---|---|---|---|
| 0 | U ↔ HP | 8.9 ± 0.01 | 6.9 ± 0.3 | 39.2 ± 1.2 | 5.0 ± 0.1 | 2.9 ± 0.1 | 8.6 ± 0.03 | 12 |
| 0.2 | U ↔ HP | 8.1 ± 0.04 | 6.4 ± 0.2 | 41.7 ± 0.8 | 5.5 ± 0.1 | 2.9 ± 0.1 | 8.6 ± 0.03 | 24 |
|  | HP ↔ PK | 3.3 ± 0.03 | 1.0 ± 0.1[e] | 0.08 ± 0.01[e] | n.d[f] | 1.0 ± 0.6 |  |  |

Data in Table 1 is represented as mean ± SEM from n traces.
[a]Distances (ΔX) are measured at 9.5 pN in CF assay.

TABLE 1-continued

Kinetics and transition distances ($\Delta x^{\ddagger}$) during folding (U→HP→PK) and unfolding (PK→HP→U) pathway

| [preQ$_1$] (□M) | Transitions | Distances $\Delta X$ (nm)$^a$ | Folding rate $k_f$ (s$^{-1}$) $^b$ | Unfolding rate $k_u$ (s$^{-1}$) $^b$ | Transition distance $\Delta x^{\ddagger}_{(U \to PK)}$ $^c$ (nm) | Transition distance $\Delta x^{\ddagger}_{(PK \to U)}$ $^c$ (nm) | F$^{eq}$ (pN) $^d$ | Number of traces (n) |
|---|---|---|---|---|---|---|---|---|

$^b$ The folding ($k_f$) and unfolding rates ($k_u$) are determined as the inverse of the mean dwell time ($<\tau>$) (Eqs. 2 & 3).
$^c$ Transition distance is determined following the relation $$k(F) = k_0 \exp\frac{F\Delta x^{\ddagger}}{k_B T},$$

where $k_0$ is the intrinsic rate, $k_B$ the Boltzmann constant and T temperature (Eq. 4). The force-dependent kinetics are shown in FIG. 4C.
$^d$ F$^{eq}$ denotes the equilibrium force, where $k_f \approx k_u$. The F$^{eq}$ is identified at the intersection of the unfolding and refolding rates. Errors are estimated by error propagation.
$^e$For HP↔PK conversion, the $k_f$ and $k_u$ indicated the ligand-association ($k_{on}$) and ligand-dissociation ($k_{off}$) kinetics, respectively. The rates ($k_{on}$, $k_{off}$) were measured in saturating ligand concentrations, where P(bound) ≈ 90%.
$^f$ n.d refers 'not-defined', since data sets did not exhibit force-dependence. Thus, Eq. 4 could not be used to extract $\Delta x^{\ddagger}$. In these cases, the reverse pathway was used to assess the transition distances. The values agree with the free energy landscape (FIG. 9B).

TABLE 2

Theoretical and observed distances for the hairpin and pseudoknot conformations in wt and mutant RNA constructs

| construct | PreQ$_1$ concentration (μM) | Folding element | Bases (nt) | Observed force, $<F_u>$ (pN) | Theoretical distance (nm) | Observed distance, $<\Delta X_u>$ (nm) | Number of traces (n) |
|---|---|---|---|---|---|---|---|
| wt | 0 | P1A | 24 | 8.7 ± 0.1 | 8.9 | 9.1 ± 0.1 | 102 |
|  | 0.2 | pseudoknot | 33 | 22.4 ± 0.2 | 15.2 | 15.7 ± 0.1 | 126 |
|  | 1 | pseudoknot | 33 | 23.8 ± 0.3 | 15.2 | 16.1 ± 0.3 | 83 |
| m1 | 0 | P1A | 24 | 10.0 ± 0.2 | 9.4 | 9.4 ± 0.3 | 145 |
|  | 0.2 | P1A | 24 | 9.1 ± 0.5 | 9.1 | 9.1 ± 0.5 | 284 |
|  | 1 | P1A | 24 | 9.7 ± 0.2 | 9.1 | 9.7 ± 0.3 | 319 |
|  | 200 | pseudoknot | 33 | 26.0 ± 04 | 16.1 | 15.9 ± 0.3 | 242 |
| m3 | 0 | P1 | 22 | 11.1 ± 0.2 | 8.8 | 9.0 ± 0.2 | 97 |
|  | 1 | P1 | 22 | 11.1 ± 0.2 | 8.8 | 8.7 ± 0.2 | 113 |
|  | 10 | pseudoknot | 33 | 22.9 ± 0.2 | 15.2 | 14.7 ± 0.2 | 100 |

Shaded rows indicate the preQ1 bound-pseudoknot receptor conformation. The percentage of bound-receptor in the ligand concentrations are shown in the figures. Clear rows indicate the unbound P1A helix.

The average rupture force, $<F_u>$ and distances, $<\Delta X_u>$ are measured in constant-speed assay. The uncertainties are represented as ±SEM from n number of traces. The observed distances ($\Delta X_u$) agreed with the theoretical values indicating that the assigned structures to the transitions are accurate within the error limit. All theoretical distances are based on the serial WLC equation (Eq. 1), wherein the inter-nucleotide distances are 0.375 nm, 0.40 nm, 0.42 nm, and 0.46 nm at 9 pN, 11 pN, 14 pN, and 22 pN, respectively. Thus, in the presence of preQ1, the observed distance indicated the 33-nt H-type pseudoknot structure, comprising of P1, P2 helices and loops L1, L2, L3 (FIG. 2B). The complete pseudoknot unfolded cooperatively in a single transition as shown in FIG. 2C. In the absence of ligand (–preQ1), the unbound RNA formed a 24-nt P1A hairpin. The structures are consistent with the NMR report.

Sensors

As discussed herein, an RNA structure, or a portion of a RNA structure, can switch between configurations or conformations in the presence of another chemical. Not only does such switching produce mechanical changes in the RNA structure, it also produces electrical changes in the RNA structure. As such, a sensor and/or sensing circuit can utilize one or more RNA structures to detect the presence and/or absence of a chemical. Stated another way, the sensor and/or sensing circuit can detect the presence and/or absence of a chemical and/or a functional group which is a part of larger chemical analyte. In at least one instance, the sensor comprises a first electrical contact, a second electrical contact, and a switching portion including the one or more RNA structures with the switching portion positioned intermediate the first electrical contact and the second electrical contact. In various instances, the first and/or second electrical contacts are placed in electrical communication with the gates of a microprocessor which is configured to detect changes in the voltage differential between the first and second electrical contacts. The microprocessor is configured such that, when the detected change in voltage potential between the first and second electrical contacts exceeds a threshold, the microprocessor generates an output signal at one or more of its output gates. Any suitable system can be placed in electrical communication with the output gate, or gates, such that the output signal is used to convey the presence of the chemical at the sensor.

The system in communication with the output gate can comprise a hand-held device, a desktop device, and/or any suitable device, and can include a display, such as an output screen and/or indicator light, for example. In various instances, the system comprises a signal transmitter configured to communicate with a remotely-positioned device. The signal transmitter can be configured to emit a wireless signal and/or a signal through a wire. In at least one instance, the RNA-based sensor comprises a signal transmitter.

In addition to or in lieu of the above, the microprocessor is configured to run an algorithm comprising one or more steps when the change in voltage differential between the first and second electrical contacts exceeds a threshold value. In various instances, such an algorithm can utilize at least one other datum to verify the presence of the chemical at the sensor and/or modify the operation of a control system.

In addition to or in lieu of detecting a change in voltage potential between the first and second electrical contacts of the sensor, the sensing circuit can be configured to detect changes in other electrical properties of a sensor. For instance, a sensor can be configured to detect changes in current, capacitance, inductance, electrochemical potential, and/or resistance, for example.

Further to the above, the sensor and/or sensing circuit comprises one or more power sources. In at least one instance, the sensor and/or sensing circuit comprises one or more batteries, for example. In certain instances, the sensor and/or sensing circuit comprises one or more photovoltaic cells, for example.

In various instances, the sensor is configured to detect the presence of more than one chemical. In at least one such instance, the sensor comprises several sensing portions in series and/or parallel with one another. The sensing portions can be configured to provide different changes in voltage potential between the first and second electrical contacts. For instance, a sensor can comprise a first sensing portion to detect a first chemical which produces a first change in voltage potential between the first and second electrical contacts and a second sensing portion to detect a second chemical which produces a second change in voltage potential between the first and second electrical contacts which is different than the first change. In various instances, the microprocessor is configured to perform a first function when the first voltage change is detected, a second function when the second voltage change is detected, and a third function when both the first and second functions are detected. In some instances, the microprocessor is configured to perform a first function until both the first and second voltage changes are detected wherein, at such point, the microprocessor performs a second, or different, function.

In various embodiments, a sensor comprises a first sensing portion configured to detect a first chemical and a second sensing portion configured to detect a second chemical. In at least one such embodiment, the first sensing portion comprises one or more electrical contacts in communication with a microprocessor and the second sensing portion comprises one or more electrical contacts in communication with the microprocessor. A sensor can comprise any suitable number of sensing portions configured to detect any suitable number of chemicals.

In various embodiments, a sensing circuit comprises a first sensor configured to detect a first chemical and a second sensor configured to detect a second chemical. A sensing circuit can comprise any suitable number of sensors configured to detect any suitable number of chemicals. The sensors in the sensing circuit can be arranged in series and/or parallel with one another.

In various embodiments, a sensor and/or sensing circuit can be configured to detect the presence of chemical contaminants, biological materials, viruses, and/or bacteria, for example. Such devices can be particularly useful in the food service industry, the medical industry, medical facilities, and/or monitoring water supplies, for example. In at least one instance, an array of sensors can be used to evaluate the presence of infections and/or other medical conditions within a small quantity of a patient's blood.

In at least one embodiment, a device comprises a RNA-based sensor which is configured to be placed in a container including perishable food. The device comprises a central processing unit (CPU) and a control system in communication with the RNA-based sensor. The device also includes a battery configured to supply power to the CPU, the control system, and/or the RNA-based sensor. The RNA-based sensor is configured to switch in the presence of one or more factors which indicates the presence of certain bacteria in spoiled food. A factor can include nucleic acid, carbohydrate, protein, and/or any other chemical of biological or non-biological origin, for example. In various instances, the voltage signal produced by the RNA-based sensor is proportional to the quantity of factors detected. In at least one instance, the RNA-based sensor generates a smaller voltage differential when a smaller quantity of factors is detected and a larger voltage differential when a larger quantity of factors is detected. The device further comprises at least one temperature sensor in communication with the CPU and/or control system. The control system is configured to detect when the temperature at the temperature sensor exceeds a threshold. The control system comprises an algorithm which is configured to evaluate the data provided by the RNA-based sensor and the temperature sensor to assess whether or not the food in the container may have become spoiled. The device further comprises an output display in communication with the CPU and/or control system which is usable by the CPU and/or control system to communicate that one or both of the thresholds has been exceeded. The algorithm can provide several stages of warnings depending on how many of the thresholds have been exceeded. For instance, the algorithm can output a first level warning if the RNA-based sensor data has exceeded a threshold but the temperature sensor data has not exceeded a threshold and a second level warning if the data from both sensors has exceeded their thresholds.

A water monitoring system can also utilize one or more RNA-based sensors. In at least one instance, the water monitoring system comprises a water inlet, a sensing portion, and a water outlet where water flows through the inlet and into the sensing portion where chemicals in the water can be detected. The sensing portion comprises a first sensing element configured to detect a first chemical, a second sensing element configured to detect a second chemical, and a third sensing element configured to detect a third chemical. The sensing elements are in signal communication with a microprocessor of the water monitoring system which comprises an on-board control system. The water monitoring system further comprises a display in signal communication with the microprocessor comprising three indicators. The microprocessor comprises an algorithm configured to activate a first indicator when the first chemical is detected by the first sensing element, a second indicator when the second chemical is detected by the second sensing element, and a third indicator when the third chemical is detected by the third sensing element. In another embodiment, the water monitoring system is configured to generate an output when one or more permutations of chemicals have been detected.

In various instances, a sensor and/or sensing circuit comprises an amplification circuit. In at least one instance, the sensing portion of a sensor generates a voltage potential which is amplified by the amplification circuit. As a result, extremely small voltages, and/or changes in voltages, in the sensor are usable by the sensing circuit to control a larger system.

A microprocessor may be any single core or multicore processor such as those known under the trade name ARM Cortex by Texas Instruments, for example. In at least one instance, the microprocessor is a LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

The methodology of switching a given hairpin conformation using small-molecule ligands is disclosed herein. Hairpins are stem-loop structures that are formed by the folding of a single-stranded RNA or DNA molecule upon itself. For a given nucleic acid sequence, it is possible to have numerous conformations that differ from each other in single base-pair, and hence numerous variations in free energy values ($\Delta G$). In other words, for a given hairpin sequence, several competitive conformational states can co-exist with equal likelihood. By using an external factor, such as a chemical moiety, one can tilt the equilibrium in favor of one conformer over others. The chemical moiety not only tilts the conformation, but continues the folding further to induce a pseudoknot conformation.

The present disclosure presents the molecular mechanism, folding pathway, kinetics, thermodynamics, and the free-energy landscape for a $preQ_1$-responsive riboswitch to illustrate how small-molecule ligands can change the hairpin conformation, and induce a desired knotted conformation for genetic-regulation and/or for detecting the presence and/or concentration of a ligand. Furthermore, by designing appropriate mutations in the hairpin sequence, the unidirectional mode of hairpin switching can be reversed or halted, which provides evidence in support of the mechanism.

The scope for applications of the techniques disclosed herein is immense, whereby hairpin conformations can be modified and regulated by the use of small molecules and/or any suitable compound. Since hairpins are involved in many gene regulatory functions, the use of controllable hairpin switching modules can open up new directions of genome engineering, whereby the hairpin structure and the functions can be modulated by small molecules and/or any suitable compound. The sensors and/or sensing systems disclosed herein can be developed in conjunction with, for example, CRISPR-CAS systems, micro RNAs and gene-silencing (miRNAs, si RNAs). As mentioned above, the $preQ_1$-responsive queC riboswitch RNA, wherein $preQ_1$ is the precursor in the formation of the nucleotide Queuosine (Q), was evaluated, but it should be understood that the present disclosure can be adapted to any suitable molecule and any suitable ligand.

Definitions

The term "comprising" or "comprises" is used in reference to compositions, methods, and respective component(s) thereof, that are essential to the invention, yet open to the inclusion of unspecified elements, whether essential or not.

The term "consisting essentially of" refers to those elements required for a given aspect. The term permits the presence of additional elements that do not materially affect the basic and novel or functional characteristic(s) of that aspect of the invention.

The term "consisting of" refers to compositions, methods, and respective components thereof as described herein, which are exclusive of any element not recited in that description of the aspect.

The singular forms "a," "an," and "the" include plural references, unless the context clearly dictates otherwise.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

Incorporation by Reference

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

The entire disclosures of the following references are incorporated by reference herein:
U.S. Patent Application Publication No. 2009/0117545.
U.S. Patent Application Publication No. 2013/0029342.
U.S. Provisional Application No. 62/376,328, filed Aug. 17, 2016.
U.S. Provisional Application No. 62/376,325, filed Aug. 17, 2016.

U.S. Provisional Application No. 62/432,077, filed Dec. 9, 2016.

U.S. Provisional Application No. 62/432,160, filed Dec. 9, 2016.

International Application No. PCT/US2017/045100, entitled MATERIALS AND METHODS FOR CONTROLLING GENE EXPRESSION, filed Aug. 2, 2017.

Pleij, C. W. Pseudoknots: a new motif in the RNA game. *Trends Biochem. Sci.* 15, 143-147 (1990).

Puglisi, J. D., Wyatt, J. R. & Tinoco I., Jr. RNA Pseudoknots. *Acc. Chem. Res.* 24, 152-158 (1991).

Han, K. & Byun, Y. PSEUDOVIEWER2: Visualization of RNA pseudoknots of any type. *Nucleic Acids Res.* 31, 3432-3440 (2003).

Leontis, N. B., Lescoute, A., & Westhof, E. The building blocks and motifs of RNA architecture. *Curr. Opin. Struct. Biol.* 16, 279-287 (2006).

Chiaruttini, C., Milet, M. & Springer, M. Translational coupling by modulation of feedback repression in the IF3 operon of *Escherichia coli*. *Proc. Natl. Acad. Sci. U. S. A.* 94, 9208-9213 (1997).

Shamoo, Y., Tam, A., Konigsberg, W. H. & Williams, K. R. Translational repression by the bacteriophage T4 gene 32 protein involves specific recognition of an RNA pseudoknot structure. *J. Mol. Biol.* 232, 89-104 (1993).

-Shen, L. X. & Tinoco, I. The structure of an RNA pseudoknot that causes efficient frameshifting in mouse mammary-tumor virus. *J. Mol. Biol.* 247, 963-978 (1995).

Giedroc, D. P. & Cornish, P. V. Frameshifting RNA pseudoknots: structure and mechanism. *Virus Res.* 139, 193-208 (2009).

Theimer, C. A., Blois, C. A. & Feigon, J. Structure of the human telomerase RNA pseudoknot reveals conserved tertiary interactions essential for function. *Mol. Cell* 17, 671-682 (2005).

Rastogi, T., Beattie, T. L., Olive, J. E. & Collins, R. A. A long-range pseudoknot is required for activity of the Neurospora VS ribozyme. *EMBO J.* 15, 2820-2825 (1996).

Ke, A. L., Zhou, K. H., Ding, F., Cate, J. H. D. & Doudna, J. A. A conformational switch controls hepatitis delta virus ribozyme catalysis. *Nature* 429, 201-205 (2004).

Theimer, C. A., & Giedroc, D. P. Equilibrium unfolding pathway of an H-type RNA pseudoknot which promotes programmed—1 ribosomal frameshifting. *J. Mol. Biol.* 289, 1283-1299 (1999).

Gluick, T. C. & Draper, D. E. Thermodynamics of folding a pseudoknotted mRNA fragment. *J. Mol. Biol.* 241, 246-262 (1994).

Isambert, H., & Siggia, E. D. Modeling RNA folding paths with pseudoknots: Application to hepatitis delta virus ribozyme. *Proc. Natl. Acad. Sci. USA* 97, 6515-6520 (2000).

Xu, X. & Chen, S-J. Kinetic mechanism of conformational switch between bistable RNA hairpins. *JACS* 134, 12499-12507 (2012).

Tinoco, I. Jr. & Bustamante, C. The effect of force on thermodynamics and kinetics of single molecule reactions. *Biophys. Chem.* 101-102, 513-533 (2002).

Savinov, A., Perez, C. F., & Block, S. M. Single-molecule studies of riboswitch folding. *Biochim. Biophys. Acta* 1839, 1030-1045 (2014).

Chandra, V., Hannan, Z., Xu, H. & Mandal, M. Single-molecule analysis reveals multi-state folding of a guanine riboswitch. *Nat. Chem. Biol.* 13, 194-201 (2017).

Elms, P. J., Chodera, J. D., Bustamante, C., & Marqusee, S. The molten globule state is unusually deformable under mechanical force. *Proc. Natl. Acad. Sci. USA* 109, 3796-3801 (2012).

Zoldák, G. & Rief, M. Force as a single-molecule probe of multidimensional protein energy landscapes. *Curr. Opin. Struct. Biol.* 23, 48-57 (2013).

Woodside, M. T., & Block, S. M. Reconstructing folding energy landscapes by single-molecule force spectroscopy. *Annu. Rev. Biophys.* 43, 19-39 (2014).

Ziegler, F., Lim, N. C. H, Mandal, S. S, Pelz, B., Ng, W-P., Schlierf, M., Jackson, S.E., Rief, M. Knotting and unknotting of a protein in single-molecule experiments. *Proc. Natl. Acad. Sci. USA* 113, 7533-7538 (2016).

Bustamante, C., Marko, J. F., Siggia, E. D. & Smith, S. Entropic Elasticity of Lambda-Phage DNA. *Science* 265, 1599-1600 (1994).

Wang, M. D., Yin, H., Landick, R., Gelles, J. & Block, S. M. Stretching DNA with Optical Tweezers. *Biophys. J.* 72,1335-1346 (1997).

Xu, H., Plaut, B., Zhu, X., Chen, M., Mavinkurve, U., Maiti, A., Song, G., Murari, K., & Mandal, M. Direct observation of folding energy landscape of RNA hairpin at mechanical loading rates. *J Phys. Chem. B* 121, 2220-2229 (2017).

Kang, M., Peterson, R. & Feigon, J. Structural Insights into riboswitch control of the biosynthesis of queuosine, a modified nucleotide found in the anticodon of tRNA. *Mol. Cell* 33, 784-790 (2009).

Klein, D. J., Edwards, T. E. & Ferre-D'Amare, A. R. Cocrystal structure of a class I preQ1 riboswitch reveals a pseudoknot recognizing an essential hypermodified nucleobase. *Nat. Struct. Mol. Biol.* 16, 343-344 (2009).

Rieder, U., Lang, K., Kreutz, C., Polacek, N. & Micura, R. Evidence for pseudoknot formation of class I preQ$_1$ riboswitch aptamers. *Chembiochem* 10, 1141-1144 (2009).

Barrick, J. E. et. al. New RNA motifs suggest an expanded scope for riboswitches in bacterial genetic control. *Proc. Natl. Acad. Sci. U.S.A.* 101, 6421-6426 (2004).

Roth, A., Winkler, W. C., Regulski, E. E., Lee, B. W., Lim, J., Jona, I., Barrick, J. E., Ritwik, A., Kim, J. N., Welz, R., Iwata-Reuyl, D. & Breaker, R. R. A riboswitch selective for the queuosine precursor preQ$_1$ contains an unusually small aptamer domain. *Nat. Struct. Mol. Biol.* 14, 308-307 (2007).

Mathews, D. H., Sabina, J., Zuker, M. & Turner, D. H. Expanded Sequence Dependence of Thermodynamic Parameters Improves Prediction of RNA Secondary Structure. *J. Mol. Biol.* 288, 911-940 (1999).

Hansen, T. M., Relhani, S. N., Oddershede, L. B. & Sørensen, M. A. Correlation between mechanical strength of messenger RNA pseudoknots and ribosomal frameshifting. *Proc. Natl. Acad. Sci. USA* 104, 5830-5835 (2007).

Chen, G., Chang, K-Y, Chou, M-Y, Bustamante, C., and Tinoco Jr., I. *Proc. Natl. Acad. Sci. USA* 106, 12706-12711 (2009).

Ritchie, D. B., Foster, D. A. N. & Woodside, M. T. Programmed—1 frameshifting efficiency correlates with RNA pseudoknot conformational plasticity, not resistance to mechanical unfolding. *Proc. Natl. Acad. Sci. USA* 109, 16167-16172 (2012).

Cho, S. S., Pincus, D. L. & Thirumalai, D. Assembly mechanisms of RNA pseudoknots are determined by the stabilities of constituent secondary structures. *Proc. Natl. Acad. Sci. U.S.A.* 106, 17349-17354 (2009).

Feng, J., Walter, N. G. & Brooks, C. L., 3$^{rd}$. Cooperative and directional folding of the preQ$_1$ riboswitch aptamer domain. *J. Am. Chem. Soc.* 133, 4196-4199 (2011).

Gong, Z., Zhao, Y., Chen, C. & Xiao, Y. Computational study of unfolding and regulation mechanism of preQ$_1$ riboswitches. *PLoS ONE* 7, e45239 (2012).

Liphardt, J., Onoa, B., Smith, S. B., Tinoco, I. Jr., & Bustamante, C. Reversible Unfolding of Single RNA Molecules by Mechanical Force. *Science* 292, 733-737 (2001).

Rieder, U., Kreutz, C. & Micura, R. Folding of a transcriptionally acting preQ$_1$ riboswitch. *Proc. Natl. Acad. Sci. U.S.A.* 107, 10804-10809 (2010).

Anderson, C. F. & Record, M. T. Jr. Polyelectrolyte theories and their applications to DNA. *Annu. Rev. Phys. Chem.* 33, 191-222 (1982).

Bacquet, R. & Rossky, P. J. Ionic distributions and competitive association in DNA/mixed salt solutions. *J. Phys. Chem.* 92, 3604-3612 (1988).

Jayaram, B. & Beveridge, D. L. Modeling DNA in aqueous solutions: theoretical and computer simulation studies on the ion atmosphere of DNA. *Annu. Rev. Biophys. Biomol. Struct.* 25, 367-394 (1996).

Korolev N., Lyubartsev, A. P., Rupprecht, A. & Nordenskiöld, L. Competitive binding of $Mg^{2+}$, $Ca^{2+}$, $Na^+$ and $K^+$ ions to DNA in oriented DNA fibers: Experimental and Monte Carlo simulation results. *Biophys. J.* 77, 2736-2749 (1999).

Jansson, P. A. Deconvolution of Images and Spectra, 2nd ed, Academic Press Inc., New York, USA (1997).

Woodside, M. T., Behnke-Parks, W. M., Larizadeh, K., Travers, K., Herschlag, D., & Block, S. M. Nanomechanical measurements of the sequence-dependent folding landscapes of single nucleic acid hairpins. *Proc. Natl. Acad. Sci. U.S.A.* 103, 6190-6195 (2006).

Gebhardt, J. C., Bornschlögl, T. & Rief, M. Full distance-resolved folding energy landscape of one single protein molecule. *Proc. Natl. Acad. Sci. U.S.A.* 107, 2013-2018 (2010).

Bell, G. I. Models for the specific adhesion of cells to cells. *Science* 200, 618-627 (1978).

Evans, E. & Ritchie, K. Dynamic strength of molecular adhesion bonds. *Biophys. J.* 72, 1541-1555 (1997).

Manosas, M., Wen, J. D., Li, P. T., Smith, S. B., Bustamante, C., Tinoco, I. Jr. & Ritort, F. Force unfolding kinetics of RNA using optical tweezers. II. Modelling experiments. *Biophys. J.* 92, 3010-3021 (2007).

Blanco, M. & Walter, N. G. Analysis of complex single-molecule FRET time trajectories. *Methods Enzymol.* 472, 153-178 (2010).

Qin, F. Restoration of single-channel currents using the segmental k-means method based on hidden Markov modeling. *Biophys. J.* 86, 1488-1501 (2004).

Rabiner, L. R. A tutorial on hidden Markov models and selected applications in speech recognition. *Proc. IEEE* 77, 257-286 (1989).

McKinney, S. A., Joo, C. & Ha, T. Analysis of single-molecule FRET trajectories using hidden Markov modeling. *Biophys. J.* 91, 1941-1951 (2006).

Kaiser, C. M., Goldman, D. H., Chodera, J. D., Tinoco, I. Jr. & Bustamante, C. The ribosome modulates nascent protein folding. *Science* 334, 1723-1727 (2011).

Cecconi, C., Shank, E. A., Bustamante, C., & Marqusee, S. Direct Observation of the Three-State Folding of a Single Protein Molecule. *Science* 309, 2057-2060 (2005).

Barrangou, R., Fremaux C., Deveau, H., Richards, M., Boyaval, P., Moineau, S., Romero, D. A., Horvath, P. CRISPR provides acquired resistance against viruses in prokaryotes. Science 2007, 315:1709-1712.

Brouns, S. J., Jore, M. M., Lundgren, M., Westra, E. R., Slijkhuis, R. J., Snijders, A. P., Dickman, M. J., Makarova, K. S., Koonin, E. V., van der Oost, J. Small CRISPR RNAs guide antiviral defense in prokaryotes. Science 2008, 321: 960-964.

Hale, C. R., Zhao, P. Olson, S., Duff, M. O., Graveley, B. R., Wells, L., Terns, R. M., Terns, M. P. RNA-guided RNA cleavage by a CRISPR RNA-Cas protein complex. Cell 2009, 139: 945-956.

Horvath, P., Barrangou, R. CRISPR/Cas, the immune system of bacteria and archaea. Science 2010, 327: 167-170.

Deltcheva, E., Chylinski, K., Sharma, C. M., Gonzales, K., Chao, Y., Pirzada Z. A., Eckert, M. R., Vogel, J., Charpentier, E. CRISPR RNA maturation by trans-encoded small RNA and host factor RNaseIII. Nature 2011, 471: 602-607.

Jiang, F., Doudna, J. A. The structural biology of CRISPR-Cas systems. Curr. Opin. Struct. Biol. 2015, 30: 100-111.

Jinek, M., Chylinski, K., Fonfara, I., Hauer, M., Doudna, J. A., Charpentier, E. A programmable dual-RNA-guide DNA endonuclease in adaptive bacterial immunity. Science 2012, 337:816-821.

Cong, L., Ran, F. A., Cox, D., Lin, S., Barretto, R., Habib, N., Hsu, P. D., Wu, X., Jiang, W., Marraffini, L. A., Zhang, F. Multiplex genome engineering using CRISPR/Cas systems. Science 2013, 339: 819-823.

Mali, P., Yang, L., Esvelt, K. M., aach, J., Guell, M., DiCarlo, J .E., Norville, J. E., Church, G. M. RNA-guided human genome engineering via Cas9. Science 2013, 339: 823-826.

Charpentier, E., Marraffini, L. A. Harnessing CRISPR-Cas 9 immunity for genetic engineering. Curr. Opin. Microbiol. 2014, 19: 114-119.

Note Regarding Illustrative Examples

While the present disclosure provides descriptions of various specific aspects for the purpose of illustrating various aspects of the present invention and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

What is claimed is:

1. A sensor, comprising:
   an electrical circuit, comprising:
   a first electrical contact;
   a second electrical contact;
   a first sensing circuit portion in electrical communication with said first electrical contact and said second electrical contact, wherein said first sensing circuit portion comprises a first RNA molecule including a riboswitch; and
   a second sensing circuit portion in electrical communication with said first electrical contact and said second electrical contact, wherein said second sensing circuit portion comprises a second RNA molecule including a riboswitch, and wherein said second RNA molecule has a different structure than said first RNA molecule.

2. The sensor of claim 1, wherein said first RNA molecule comprises a hairpin, wherein said hairpin is configured to switch between a first conformation and a second conformation, wherein a first voltage potential is present between said first and second electrical contacts when said hairpin is in said first conformation, and wherein a second voltage potential, which is different than said first voltage potential, is present between said first and second electrical contacts when said hairpin is in said second conformation.

3. The sensor of claim 2, wherein said second RNA molecule comprises a second hairpin, wherein said second hairpin is configured to switch between an initial conformation and a changed conformation, wherein a voltage potential is present between said first and second electrical contacts when said second hairpin is in said initial conformation, and wherein a different voltage potential is present between said first and second electrical contacts when said second hairpin is in said changed conformation.

4. The sensor of claim 1, wherein the electrical circuit further comprises a CPU and a temperature sensing circuit in communication with the CPU, wherein the CPU is configured to detect when the temperature at the temperature sensing circuit exceeds a threshold.

5. The sensor of claim 4, wherein the CPU is configured to detect when data from one of said first sensing portion and said second sensing portion exceeds a threshold, and wherein the CPU comprises an algorithm which is configured to evaluate the data provided by said temperature sensing circuit and said first and second sensing portions.

6. The sensor of claim 5, wherein the algorithm provides several stages of warnings depending on how many of the thresholds have been exceeded.

7. The sensor of claim 6, wherein the algorithm outputs a first level warning if data from one of said sensing portions has exceeded a threshold but the temperature sensing circuit data has not exceeded a threshold and a second level warning if data from one of said sensor portions and the temperature sensing circuit has exceeded their thresholds.

8. The sensor of claim 1, further comprising a signal transmitter configured to communicate with a computer system positioned remotely with respect to the sensor.

9. The sensor of claim 1, further comprising a battery.

10. The sensor of claim 1, wherein said riboswitch of said first RNA molecule is configured to switch in the presence of one or more factors which indicates the presence of certain bacteria in spoiled food.

11. The sensor of claim 10, wherein the factor can include nucleic acid, carbohydrate, protein, and/or any other chemical of biological or non-biological origin.

* * * * *